United States Patent
el Kaliouby et al.

(10) Patent No.: US 10,843,078 B2
(45) Date of Patent: *Nov. 24, 2020

(54) AFFECT USAGE WITHIN A GAMING CONTEXT

(71) Applicant: Affectiva, Inc., Waltham, MA (US)

(72) Inventors: Rana el Kaliouby, Milton, MA (US); Panu James Turcot, San Francisco, CA (US); Forest Jay Handford, Berlin, MA (US); Daniel Bender, Cambridge, MA (US); Rosalind Wright Picard, Newtonville, MA (US); Richard Scott Sadowsky, Sturbridge, MA (US); Oliver Orion Wilder-Smith, Holliston, MA (US)

(73) Assignee: Affectiva, Inc., Boston, MA (US)

( * ) Notice: Subject to any disclaimer, the term of this patent is extended or adjusted under 35 U.S.C. 154(b) by 1259 days.

This patent is subject to a terminal disclaimer.

(21) Appl. No.: 15/012,246

(22) Filed: Feb. 1, 2016

(65) Prior Publication Data

US 2016/0144278 A1 May 26, 2016

Related U.S. Application Data

(63) Continuation-in-part of application No. 13/366,648, filed on Feb. 6, 2012, now Pat. No. 9,247,903, which
(Continued)

(51) Int. Cl.
*A63F 13/58* (2014.01)
*A63F 13/655* (2014.01)
(Continued)

(52) U.S. Cl.
CPC .............. *A63F 13/58* (2014.09); *A61B 5/165* (2013.01); *A61B 5/7271* (2013.01);
(Continued)

(58) Field of Classification Search
None
See application file for complete search history.

(56) References Cited

U.S. PATENT DOCUMENTS

| 3,034,500 | A | 5/1962 | Backster, Jr. |
| 3,548,806 | A | 12/1970 | Fisher |

(Continued)

FOREIGN PATENT DOCUMENTS

| JP | 08115367 | 7/1996 |
| KR | 10-2005-0021759 A | 3/2005 |

(Continued)

OTHER PUBLICATIONS

Rana Ayman El Kaliouby, Mind-reading machines: automated inference of complex mental states, Jul. 2005, University of Cambridge, Cambridge, United Kingdom.
(Continued)

*Primary Examiner* — Jason T Yen
(74) *Attorney, Agent, or Firm* — Adams Intellex, PLC

(57) ABSTRACT

Mental state data is collected as a person interacts with a game played on a machine. The mental state data includes facial data, where the facial data includes facial regions or facial landmarks. The mental state data can include physiological data and actigraphy data. The mental state data is analyzed to produce mental state information. Mental state data and/or mental state information can be shared across a social network or a gaming community. The affect of the person interacting with the game can be represented to the social network or gaming community in the form of an avatar. Recommendations based on the affect resulting from the analysis can be made to the person interacting with the game. Mental states are analyzed locally or via a web services. Based on the results of the analysis, the game with which the person is interacting is modified.

27 Claims, 17 Drawing Sheets

Related U.S. Application Data is a continuation-in-part of application No. 13/153,745, filed on Jun. 6, 2011, now abandoned, said application No. 13/366,648 is a continuation-in-part of application No. 13/297,342, filed on Nov. 16, 2011, now abandoned, application No. 15/012,246, which is a continuation-in-part of application No. 14/961,279, filed on Dec. 7, 2015, now Pat. No. 10,143,414, which is a continuation-in-part of application No. 14/064,136, filed on Oct. 26, 2013, now Pat. No. 9,204,836, said application No. 14/961,279 is a continuation-in-part of application No. 13/153,745, filed on Jun. 6, 2011, now abandoned, said application No. 14/961,279 is a continuation-in-part of application No. 14/796,419, filed on Jul. 10, 2015, now abandoned, which is a continuation-in-part of application No. 13/153,745, filed on Jun. 6, 2011, now abandoned, said application No. 14/796,419 is a continuation-in-part of application No. 14/460,915, filed on Aug. 15, 2014, now abandoned, said application No. 14/796,419 is a continuation-in-part of application No. 13/153,745, filed on Jun. 6, 2011, now abandoned, application No. 15/012,246, which is a continuation-in-part of application No. 13/768,288, filed on Feb. 15, 2013, now abandoned, application No. 15/012,246, which is a continuation-in-part of application No. 13/886,249, filed on May 2, 2013, now abandoned, which is a continuation-in-part of application No. 13/153,745, filed on Jun. 6, 2011, now abandoned, application No. 15/012,246, which is a continuation-in-part of application No. 14/214,751, filed on Mar. 15, 2014, now abandoned, which is a continuation-in-part of application No. 13/153,745, filed on Jun. 6, 2011, now abandoned, application No. 15/012,246, which is a continuation-in-part of application No. 13/867,049, filed on Apr. 20, 2013, now abandoned, which is a continuation-in-part of application No. 13/153,745, filed on Jun. 6, 2011, now abandoned, said application No. 13/867,049 is a continuation-in-part of application No. 13/708,214, filed on Dec. 7, 2012, now abandoned.

(60) Provisional application No. 61/719,383, filed on Oct. 27, 2012, provisional application No. 62/217,872, filed on Sep. 12, 2015, provisional application No. 62/222,518, filed on Sep. 23, 2015, provisional application No. 62/265,937, filed on Dec. 10, 2015, provisional application No. 62/273,896, filed on Dec. 31, 2015, provisional application No. 61/439,913, filed on Feb. 6, 2011, provisional application No. 61/447,089, filed on Feb. 27, 2011, provisional application No. 61/447,464, filed on Feb. 28, 2011, provisional application No. 61/467,209, filed on Mar. 24, 2011, provisional application No. 61/549,560, filed on Oct. 20, 2011, provisional application No. 61/568,130, filed on Dec. 7, 2011, provisional application No. 61/580,880, filed on Dec. 28, 2011, provisional application No. 61/581,913, filed on Dec. 30, 2011, provisional application No. 61/352,166, filed on Jun. 7, 2010, provisional application No. 61/388,002, filed on Sep. 30, 2010, provisional application No. 61/414,451, filed on Nov. 17, 2010, provisional application No. 61/439,913, filed on Feb. 6, 2011, provisional application No. 62/128,974, filed on Mar. 5, 2015, provisional application No. 61/747,651, filed on Dec. 31, 2012, provisional application No. 61/747,810, filed on Dec. 31, 2012, provisional application No. 61/793,761, filed on Mar. 15, 2013, provisional application No. 61/790,461, filed on Mar. 15, 2013, provisional application No. 61/789,038, filed on Mar. 15, 2013, provisional application No. 61/798,731, filed on Mar. 15, 2013, provisional application No. 61/844,478, filed on Jul. 10, 2013, provisional application No. 62/023,800, filed on Jul. 11, 2014, provisional application No. 62/047,508, filed on Sep. 8, 2014, provisional application No. 62/082,579, filed on Nov. 20, 2014, provisional application No. 61/867,007, filed on Aug. 16, 2013, provisional application No. 61/924,252, filed on Jan. 7, 2014, provisional application No. 61/916,190, filed on Dec. 14, 2013, provisional application No. 61/927,481, filed on Jan. 15, 2014, provisional application No. 61/953,878, filed on Mar. 16, 2014, provisional application No. 61/972,314, filed on Mar. 30, 2014, provisional application No. 61/618,750, filed on Mar. 31, 2012, provisional application No. 61/641,852, filed on May 2, 2012, provisional application No. 61/636,634, filed on Apr. 21, 2012.

(51) Int. Cl.
| | |
|---|---|
| *A63F 13/825* | (2014.01) |
| *A63F 13/213* | (2014.01) |
| *G06F 3/01* | (2006.01) |
| *G07F 17/32* | (2006.01) |
| *A61B 5/00* | (2006.01) |
| *A61B 5/16* | (2006.01) |
| *G16H 20/70* | (2018.01) |
| *G16H 50/30* | (2018.01) |
| *G16H 40/63* | (2018.01) |

(52) U.S. Cl.
CPC .......... *A63F 13/213* (2014.09); *A63F 13/655* (2014.09); *A63F 13/825* (2014.09); *G06F 3/011* (2013.01); *G06F 3/015* (2013.01); *G07F 17/3206* (2013.01); *G07F 17/3239* (2013.01); *G16H 20/70* (2018.01); *G16H 40/63* (2018.01); *G16H 50/30* (2018.01); *A63F 2250/1031* (2013.01); *A63F 2250/26* (2013.01); *G06F 2203/011* (2013.01)

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |

(56) References Cited

U.S. PATENT DOCUMENTS

| | | |
|---|---|---|
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,091,334 A | 7/2000 | Galiana et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ball et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,758,746 B1 | 7/2004 | Hunter et al. |
| 6,792,458 B1 | 9/2004 | Muret et al. |
| 6,847,376 B2 | 1/2005 | Engeldrum et al. |
| 7,003,135 B2 | 2/2006 | Hsieh et al. |
| 7,013,478 B1 | 3/2006 | Hendricks et al. |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,747,801 B2 | 6/2010 | Han et al. |
| 7,757,171 B1 | 7/2010 | Wong et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 8,010,458 B2 | 8/2011 | Galbreath et al. |
| 8,022,831 B1 | 9/2011 | Wood-Eyre |
| 8,219,438 B1 | 7/2012 | Moon et al. |
| 8,401,248 B1 | 3/2013 | Moon et al. |
| 8,442,638 B2 | 5/2013 | Libbus et al. |
| 8,522,779 B2 | 9/2013 | Lee et al. |
| 8,600,120 B2 | 12/2013 | Gonion et al. |
| 8,640,021 B2 | 1/2014 | Perez et al. |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1 | 11/2002 | Eshelman |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0093784 A1 | 5/2003 | Dimitrova et al. |
| 2003/0182123 A1 | 9/2003 | Mitsuyoshi |
| 2003/0191682 A1 | 10/2003 | Shepard et al. |
| 2003/0191816 A1 | 10/2003 | Landress et al. |
| 2004/0181457 A1 | 9/2004 | Biebesheimer |
| 2005/0187437 A1 | 8/2005 | Matsugu |
| 2005/0283055 A1 | 12/2005 | Shirai et al. |
| 2005/0289582 A1 | 12/2005 | Tavares et al. |
| 2006/0019224 A1 | 1/2006 | Behar et al. |
| 2006/0143647 A1 | 6/2006 | Bill |
| 2006/0170945 A1 | 8/2006 | Bill |
| 2006/0235753 A1 | 10/2006 | Kameyama |
| 2007/0113181 A1 | 5/2007 | Blattner et al. |
| 2007/0167689 A1 | 7/2007 | Ramadas et al. |
| 2007/0173733 A1 | 7/2007 | Le et al. |
| 2007/0239787 A1 | 10/2007 | Cunningham et al. |
| 2007/0255831 A1 | 11/2007 | Hayashi et al. |
| 2007/0265507 A1 | 11/2007 | de Lemos |
| 2007/0299964 A1 | 12/2007 | Wong et al. |
| 2008/0001951 A1* | 1/2008 | Marks ............... A63F 13/06 345/474 |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0184170 A1 | 7/2008 | Periyalwar |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1 | 11/2008 | Kurtz et al. |
| 2008/0318673 A1* | 12/2008 | Rofougaran ....... A63F 13/212 463/29 |
| 2009/0002178 A1 | 1/2009 | Guday et al. |
| 2009/0006206 A1 | 1/2009 | Groe |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0150919 A1 | 6/2009 | Lee et al. |
| 2009/0164132 A1 | 6/2009 | Jung et al. |
| 2009/0193344 A1 | 7/2009 | Smyers |
| 2009/0210290 A1 | 8/2009 | Elliott et al. |
| 2009/0217315 A1 | 8/2009 | Malik et al. |
| 2009/0259518 A1 | 10/2009 | Harvey |
| 2009/0270170 A1* | 10/2009 | Patton ............... A63F 13/10 463/36 |
| 2009/0271417 A1 | 10/2009 | Toebes et al. |
| 2009/0285456 A1 | 11/2009 | Moon et al. |
| 2009/0299840 A1 | 12/2009 | Smith |

(56) References Cited

U.S. PATENT DOCUMENTS

| | | | |
|---|---|---|---|
| 2009/0300525 A1 | 12/2009 | Jolliff et al. | |
| 2010/0070523 A1 | 3/2010 | Delgo et al. | |
| 2010/0099955 A1 | 4/2010 | Thomas et al. | |
| 2010/0141663 A1* | 6/2010 | Becker | G06T 13/40 345/473 |
| 2010/0153868 A1* | 6/2010 | Allen | G06T 13/40 715/764 |
| 2010/0266213 A1 | 10/2010 | Hill | |
| 2010/0274847 A1 | 10/2010 | Anderson et al. | |
| 2010/0287510 A1* | 11/2010 | Cragun | G06Q 10/10 715/848 |
| 2010/0306671 A1* | 12/2010 | Mattingly | G06Q 10/10 715/753 |
| 2010/0324437 A1 | 12/2010 | Freeman | |
| 2011/0126226 A1 | 5/2011 | Makhlouf | |
| 2011/0134026 A1 | 6/2011 | Kang et al. | |
| 2011/0143728 A1 | 6/2011 | Holopainen et al. | |
| 2011/0144971 A1 | 6/2011 | Danielson | |
| 2011/0196855 A1 | 8/2011 | Wable et al. | |
| 2011/0207100 A1* | 8/2011 | Brokken | G06F 3/011 434/236 |
| 2011/0231240 A1 | 9/2011 | Schoen et al. | |
| 2011/0251493 A1 | 10/2011 | Poh et al. | |
| 2011/0263946 A1 | 10/2011 | el Kaliouby et al. | |
| 2011/0275432 A1* | 11/2011 | Lutnick | G07F 17/3232 463/25 |
| 2012/0324491 A1 | 12/2012 | Bathiche et al. | |
| 2013/0023337 A1 | 1/2013 | Bowers et al. | |
| 2013/0116587 A1 | 5/2013 | Sornmo et al. | |
| 2013/0197409 A1 | 8/2013 | Baxter et al. | |
| 2014/0172910 A1 | 6/2014 | Jung et al. | |
| 2016/0104486 A1 | 4/2016 | Penilla et al. | |
| 2017/0003784 A1 | 1/2017 | Garg et al. | |

FOREIGN PATENT DOCUMENTS

| | | |
|---|---|---|
| KR | 10-2008-0016303 A | 2/2008 |
| KR | 1020100048688 A | 5/2010 |
| WO | WO 2011/045422 A1 | 4/2011 |

OTHER PUBLICATIONS

International Search Report dated Nov. 14, 2011 for PCT/US2011/039282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming HE, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

Albiol, Alberto, et al. "Face recognition using HOG-EBGM." Pattern Recognition Letters 29.10 (2008): 1537-1543.

Fasel, B. (Aug. 2002). Robust face analysis using convolutional neural networks. In Object recognition supported by user interaction for service robots (vol. 2, pp. 40-43). IEEE.

Matsugu, M., Mori, K., Mitari, Y., & Kaneda, Y. (2003). Subject independent facial expression recognition with robust face detection using a convolutional neural network. Neural Networks, 16(5-6), 555-559.

* cited by examiner

AFFECT USAGE WITHIN A GAMING CONTEXT

RELATED APPLICATIONS

This application claims the benefit of U.S. provisional patent applications "Viewership Analysis Based on Facial Evaluation" Ser. No. 62/128,974, filed Mar. 5, 2015, "Mental State Event Signature Usage" Ser. No. 62/217,872, filed Sep. 12, 2015, "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 10, 2015, and "Image Analysis Using Sub-Sectional Component Evaluation To Augment Classifier Usage" Ser. No. 62/273,896, filed Dec. 31, 2015. This application is also a continuation-in-part of U.S. patent application "Using Affect Within A Gaming Context" Ser. No. 13/366,648, filed Feb. 6, 2012, which claims the benefit of U.S. provisional patent applications "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, "Baseline Face Analysis" Ser. No. 61/467,209, filed Mar. 24, 2011, "Mental State Analysis of Voters" Ser. No. 61/549,560, filed Oct. 20, 2011, "Mental State Evaluation Learning for Advertizing" Ser. No. 61/568,130, filed Dec. 7, 2011, "Affect Based Concept Testing" Ser. No. 61/580,880, filed Dec. 28, 2011, and "Affect Based Evaluation of Advertisement Effectiveness" Ser. No. 61/581,913, filed Dec. 30, 2011 and is also a continuation-in-part of U.S. patent application "Mental State Analysis Using Web Services" Ser. No. 13/153,745, filed Jun. 6, 2011 which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011 and is also a continuation-in-part of U.S. patent application "Sharing Affect Across a Social Network" Ser. No. 13/297,342, filed Nov. 16, 2011 which claims the benefit of U.S. provisional patent applications "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, "Baseline Face Analysis" Ser. No. 61/467,209, filed Mar. 24, 2011, and "Mental State Analysis of Voters" Ser. No. 61/549,560, filed Oct. 20, 2011.

This application is also a continuation-in-part of U.S. patent application "Sporadic Collection with Mobile Affect Data" Ser. No. 14/961,279, filed Dec. 7, 2015 which is a continuation in part of U.S. patent application "Sporadic Collection of Mobile Affect Data" Ser. No. 14/064,136, filed Oct. 26, 2013, which claims the benefit of U.S. provisional patent applications "Sporadic Collection of Mobile Affect Data" Ser. No. 61/719,383, filed Oct. 27, 2012, "Optimizing Media Based on Mental State Analysis" Ser. No. 61/747,651, filed Dec. 31, 2012, "Collection of Affect Data from Multiple Mobile Devices" Ser. No. 61/747,810, filed Dec. 31, 2012, "Mental State Analysis Using Heart Rate Collection Based on Video Imagery" Ser. No. 61/793,761, filed Mar. 15, 2013, "Mental State Data Tagging for Data Collected from Multiple Sources" Ser. No. 61/790,461, filed Mar. 15, 2013, "Mental State Analysis Using Blink Rate" Ser. No. 61/789,038, filed Mar. 15, 2013, "Mental State Well Being Monitoring" Ser. No. 61/798,731, filed Mar. 15, 2013, and "Personal Emotional Profile Generation" Ser. No. 61/844,478, filed Jul. 10, 2013 and is also a continuation-in-part of U.S. patent application "Mental State Analysis Using Web Services" Ser. No. 13/153,745, filed Jun. 6, 2011 which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011 and is also a continuation-in-part of U.S. patent application "Mental State Event Definition Generation" Ser. No. 14/796,419, filed Jul. 10, 2015, which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based on Facial Evaluation" Ser. No. 62/128,974, filed Mar. 5, 2015. The application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. The application "Sporadic Collection With Mobile Affect Data" Ser. No. 14/961,279, filed Dec. 7, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No.

62/023,800, filed Jul. 11, 2014 and is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

This application is also a continuation-in-part of U.S. patent application "Predicting Purchase Intent Based on Affect" Ser. No. 13/768,288, filed Feb. 15, 2013, which claims the benefit of U.S. provisional patent application "Predicting Purchase Intent Based on Affect" Ser. No. 61/618,750, filed Mar. 31, 2012.

This application is also a continuation-in-part of U.S. patent application "Mental State Analysis Using Wearable-Camera Devices" Ser. No. 13/886,249, filed May 2, 2013, which claims the benefit of U.S. provisional patent application "Ear-Mounted Mental State Analysis Device" Ser. No. 61/641,852, filed May 2, 2012 which is also a continuation-in-part of U.S. patent application "Mental State Analysis Using Web Services" Ser. No. 13/153,745, filed Jun. 6, 2011 which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

This application is also a continuation-in-part of U.S. patent application "Mental State Well Being Monitoring" Ser. No. 14/214,751, filed Mar. 15, 2014, which claims the benefit of U.S. provisional patent applications "Mental State Well Being Monitoring" Ser. No. 61/798,731, filed Mar. 15, 2013, "Mental State Analysis Using Heart Rate Collection Based on Video Imagery" Ser. No. 61/793,761, filed Mar. 15, 2013, "Mental State Analysis Using Blink Rate" Ser. No. 61/789,038, filed Mar. 15, 2013, "Mental State Data Tagging for Data Collected from Multiple Sources" Ser. No. 61/790,461, filed Mar. 15, 2013, "Personal Emotional Profile Generation" Ser. No. 61/844,478, filed Jul. 10, 2013, "Heart Rate Variability Evaluation for Mental State Analysis" Ser. No. 61/916,190, filed Dec. 14, 2013, "Mental State Analysis Using an Application Programming Interface" Ser. No. 61/924,252, filed Jan. 7, 2014, and "Mental State Analysis for Norm Generation" Ser. No. 61/927,481, filed Jan. 15, 2014 and is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

This application is also a continuation-in-part of U.S. patent application "Sales Projections Based on Mental States" Ser. No. 13/867,049, filed Apr. 20, 2013, which claims the benefit of U.S. provisional patent applications "Sales Projections Based on Mental States" Ser. No. 61/636,634, filed Apr. 21, 2012 and "Optimizing Media Based on Mental State Analysis" Ser. No. 61/747,651, filed Dec. 31, 2012 and is also a continuation-in-part of U.S. patent application "Mental State Analysis Using Web Services" Ser. No. 13/153,745, filed Jun. 6, 2011 which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. The application "Sales Projections Based on Mental States" Ser. No. 13/867,049, filed Apr. 20, 2013 is also a continuation-in-part of U.S. patent application "Affect Based Evaluation of Advertisement Effectiveness" Ser. No. 13/708,214, filed Dec. 7, 2012 which claims the benefit of U.S. provisional patent applications "Mental State Evaluation Learning for Advertising" Ser. No. 61/568,130, filed Dec. 7, 2011 and "Affect Based Evaluation of Advertisement Effectiveness" Ser. No. 61/581,913, filed Dec. 30, 2011.

Each of the foregoing applications is hereby incorporated by reference in its entirety.

FIELD OF INVENTION

This application relates generally to analysis of mental states and more particularly to using affect within a gaming context.

BACKGROUND

Computer gaming is an enormously popular activity that is enjoyed by a large portion of the population. Children, teenagers, and even adults have all enjoyed video gaming as a pastime, for educational purposes, for training, for exercise, and the like. Computer games may include a wide range of genres such as sporting events and activities, automotive driving and racing, aircraft and spacecraft flight, fantasy themes, updated board games, social games and activities, military-oriented and "first person shooter" games, etc. Various age groups enjoy creative and engaging computer gaming activities.

Many computer games incorporate a competitive, multi-player component into their design. This aspect of the games heightens competition and has led to shared enjoyment of a game by two or more players. In the past, two or more players may have been collocated with a computer game, but it is now more common that the multiplicity of players is dispersed across a large geographical area. In some cases, the players may be dispersed across multiple time zones around the globe. Nonetheless, because of the immersive nature of video games, there is a real and vibrant sense of community that can develop among gamers. Individuals in the community can work on game strategy, contribute to game enhancements, and even develop interpersonal friendships that transcend the gaming experience. The gaming environment has become a way for people and teams of people to have interpersonal interactions with likeminded players. Gamers want to share various aspects of their gaming experiences with each other in order to feel that they are an integral part of the game. As a result, game players can spend a tremendous amount of time involved with these games.

Computer gaming enthusiasts concur that the more immersive the computer game, the greater the degree of satisfaction that can be derived from it. Thus, computer game developers strive to create an immersive experience. Sight, sound, physical gestures, and now various creative controlling schemes all contribute to the sense that the gamer has become an integral part of the game. Thus, the more interactive the interface, the greater and more enjoyable the gaming experience.

Many types of computer interfaces and enhancements exist which can be used to interact with and control a computer game. For example, a screen or multiple screens used by the ubiquitous graphical user interfaces (GUI) may be substituted with a touch screen, thus allowing the user to manipulate the game by touch. This latter adaptation is common with handheld devices. Interfaces allow manipulation of simulated objects and their properties. Tangible user interfaces enable touch and physical feedback (i.e. force feedback) for working in physical environments or their elements. Task-focused interfaces are enhancements that address the "information overload" problem by allowing the user to focus on tasks rather than a multitude of specific elements. Zooming interfaces allow for changes in levels of detail about objects, thus permitting zooming in on specific aspects from sets of elements.

Another interface class uses sensors to collect inputs. For example, an interface may include user voice activation that permits information capture, control, etc. Further, motion recognition is becoming a popular gaming interface. Such activity-interface devices may include a gamepad, paddle, trackball, joystick, a throttle, steering wheels, aircraft type yokes (oriented to aircraft control), pedals (vehicle control), a keyboard and mouse, a touch screen, motion sensing, and a light gun. Other gesture recognition devices are purpose-oriented, such as pinball controllers, dance pads, balance boards, rhythm game devices (keyboards, guitars, drums, microphones, etc.), buzzers (like those used in game shows), sports equipment (fishing rods, tennis racquets), and the like.

SUMMARY

Analysis of people as they interact with a gaming environment be can be performed by gathering mental states through evaluation of facial expressions, head gestures, and physiological conditions. This analysis can be used to inform others in a social network of the mental states of people interacting with the game. The analysis can also be used to modify the gaming experience. A computer implemented method for gaming is disclosed comprising: collecting mental state data, wherein the mental state data includes facial data, captured by a webcam, of an individual while the individual is involved in a game; analyzing the mental state data to produce mental state information; and modifying the game based on the mental state information, wherein the modifying the game includes changing tasks with which the individual is presented, based on a threshold. A webcam can be further used to capture one the physiological data. The method can further comprise inferring mental states with regard to the game based on the mental state data which was collected wherein the mental states include one or more of frustration, confusion, disappointment, hesitation, cognitive overload, focusing, engagement, attention, boredom, exploration, confidence, trust, delight, disgust, skepticism, doubt, satisfaction, excitement, laughter, calmness, stress, and curiosity. The game can be within an electronic gaming environment. The modifying the game can include modifying an avatar that represents the individual. The avatar can be animated based on the mental state information.

The modifying the game can include changing tasks with which the individual is presented. The changing tasks can include making the game harder. The mental state information can include an indication of boredom. The changing tasks can include making the game easier. The mental state information can include an indication of frustration. The game can be a multiplayer game. The modifying the game can include modifying an avatar that represents a group of people who are playing the multiplayer game. The avatar can represent a collective mental state for the group of people. The multiplayer game can include requiring players to imitate a face. The multiplayer game can include an objective of achieving a collective mental state. The multiplayer game can include an objective of avoiding a collective mental state. The game can include an objective of achieving a mental state by the individual. The game can include an objective of avoiding a mental state by the individual. The method can further comprise developing a mental state for a computer generated player. The computer generated player can compete against the individual. The computer generated player can be on a team with the individual.

In embodiments, a computer implemented method for gaming comprises: collecting mental state data of an individual while the individual is involved in a gaming environment; analyzing the mental state data to produce mental state information; and sharing the mental state information across a social network. In some embodiments, a computer implemented method for gaming comprises: collecting mental state data of an individual while the individual is involved in a game within a gaming environment; analyzing, using a web services server, the mental state data to produce mental state information; and displaying the mental state information in a visualization.

In embodiments, a computer program product stored on a non-transitory computer-readable medium for gaming comprises: code for collecting mental state data of an individual while the individual is involved in a game; code for analyzing, using a web services server, the mental state data to produce mental state information; and code for modifying the game based on the mental state information. In some embodiments, a computer system for gaming comprises: a memory for storing instructions; one or more processors attached to the memory wherein the one or more processors are configured to: collect mental state data of an individual while the individual is involved in a game; analyze, using a web services server, the mental state data to produce mental state information; and modify the game based on the mental state information.

Various features, aspects, and advantages of numerous embodiments will become more apparent from the following description.

BRIEF DESCRIPTION OF THE DRAWINGS

The following detailed description of certain embodiments may be understood by reference to the following figures wherein.

DETAILED DESCRIPTION

The present disclosure provides a description of various methods and systems for analyzing people's mental states as they interact with a gaming environment. Knowledge and use of players' emotions in the midst of gaming can provide enormous possibilities. Historically, board games were played around a dining room or coffee table. With the advent of modern electronic gaming, participants are now located at significant distance from one another. Due to this distance, gamers cannot obviously perceive how opponents are feeling. With the disclosed concept, gamers can now understand the emotions their opponents or teammates are experiencing. Affect can be communicated across a distance. Beyond that, an electronic game can perceive a person's mental states and adapt aspects of the game accordingly.

A mental state can be an emotional state or a cognitive state. Examples of emotional states include happiness or sadness. Examples of cognitive states include concentration or confusion. Observing, capturing, and analyzing these mental states can yield significant information about people's reactions to a game that far exceed previous capabilities in gaming. Analysis of the mental states can be provided by web services where modifications to the games can also be provided. Some terms commonly used in evaluation of mental states are arousal and valence. Arousal is an indication on the amount of activation or excitement of a person. Valence is an indication on whether a person is positively or negatively disposed. Affect can include analysis of arousal and valence. Affect can also include facial analysis for expressions such as smiles or brow furrowing.

Figure 1:
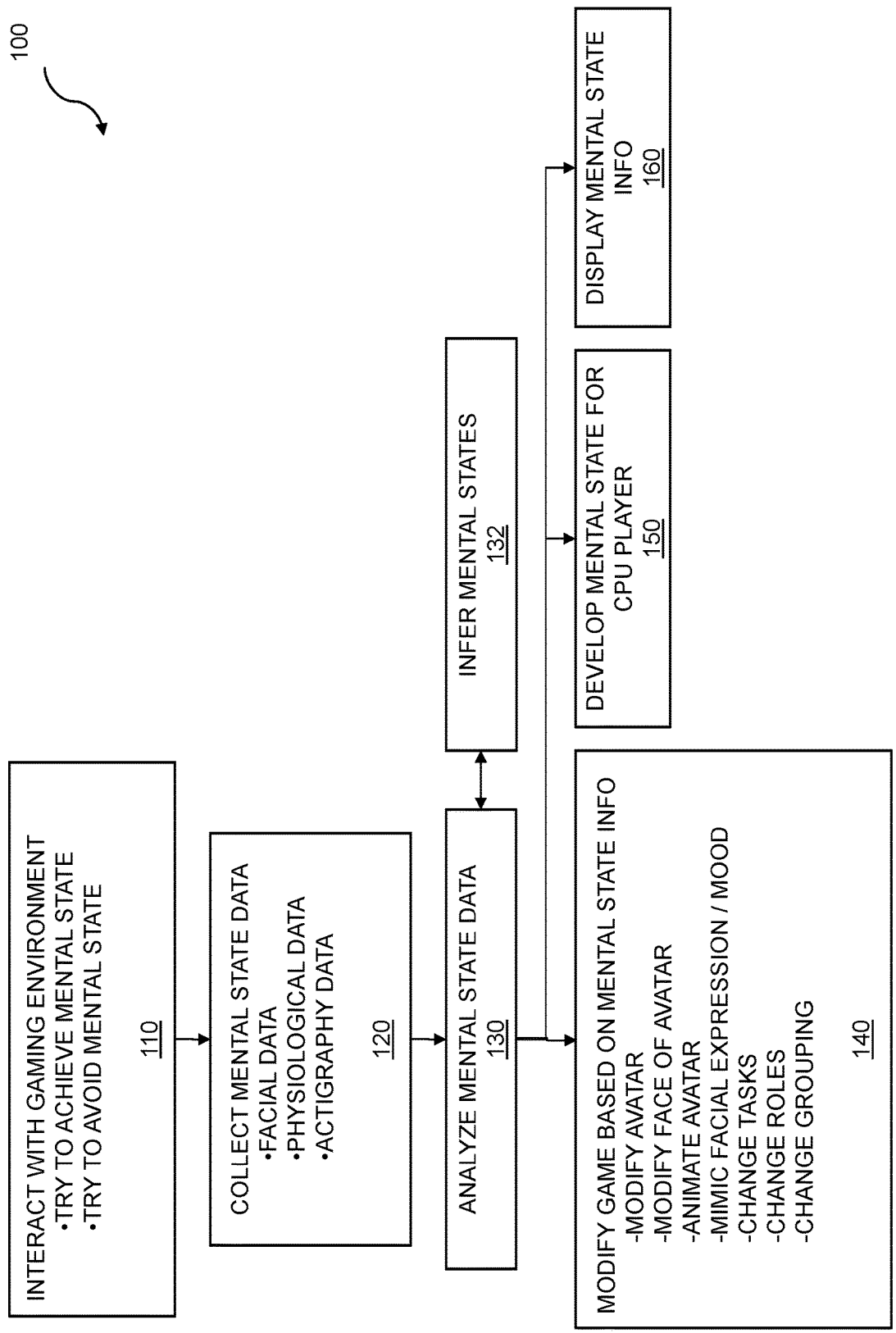
FIG. 1 is a flow diagram representing gaming interaction.

FIG. 1 is a flow diagram representing gaming interaction. A flow 100 is shown for a computer implemented method for gaming. The flow 100 begins with an individual or group of people interacting with a gaming environment 110. In the gaming environment, an individual can play a game that can be one of a computer game, a video game, a personal game, a kinetic game, or the like. The game could be for entertainment, for education, for training, for simulating an experience, and so on. In some cases, the game can be a professional training aid for pilots, astronauts, doctors, surgeons, psychologists, managers, teachers, and so on. In some cases, the game can be part of a therapeutic exercise to help in mental health wellness.

The game can be a previously developed game or a game especially developed to take advantage of mental state capabilities. In some embodiments, the game can include requiring one or more players to imitate a face. Based on facial expression analysis, a match or a close match to the face to imitate can be determined. The face to be imitated can be a physical manifestation of a certain mental state such as happy, sad, or the like. In some cases, the face to be imitated can include an expression designed to intimidate, persuade, be compassionate, be aloof, etc. The game can include as an objective the achievement of a mental state by the individual playing the game. This type of game can be used therapeutically by encouraging the individual to reach a state of contentedness or happiness as opposed to being depressed. In some embodiments, the game includes as an objective the individual's avoidance of a particular mental state. In some cases, a multiplayer game can include as an objective the individual's achievement of a collective mental or, if a group of players are playing together, the group's concurrent achievement of a certain mental state. Alternatively, the game's objective can be for the individual to provoke a certain reaction in another person or group of people. In some cases, the objective can be for the other person or group to achieve a certain mental state. In some embodiments, the game can include as an objective a group of players' collective avoidance of a certain mental state. For example, the game can include a comedic sequence with the collective objective set as avoiding smiling or laughing. In this case, there could be a contest between multiple teams to see which team can be the most stoic.

The flow 100 continues with collecting mental state data 120 of an individual while the individual is involved in a game. The collecting of mental state data can comprise collecting one or more of facial data, physiological data, and actigraphy data. The mental state data includes facial data, captured by a webcam, of an individual while the individual is involved in a game. The mental state data can be collected by a gaming machine which is part of the gaming environment. Alternatively, the mental state data can be collected by a peripheral device or computer which has access to the individual. In some embodiments, a webcam can be used to capture one or more of the facial data and the physiological data. In embodiments, the physiological data and actigraphy data can be obtained from one or more biosensors attached to an individual.

The flow 100 continues with analyzing, using a web services server, the mental state data 130 to produce mental state information. The web services server can be a remote computer from the game machine. The server can provide game information to the gaming machine and also can facilitate play between multiple players. In embodiments, the flow includes aggregating the mental state information on a plurality of people who play the multiplayer game. The analyzing can include aggregating mental state information with others who are playing or have played the game. While mental state data can be raw data, mental state information can include the raw data or information derived from the raw data. The mental state information can include all of the mental state data or a subset thereof. The mental state information can include valence and arousal. The mental state information can include information on the mental states experienced by a gamer. Some analysis of the mental state data can be performed on a client computer before the data is uploaded; analysis of the data can also be performed on a server computer. Analysis of the mental state data can take many forms and can be based on one person or a plurality of people. In some embodiments, the mental state information is propagated to a social network. Through the social network others can be made aware of an individual's affect as they interact with the gaming environment. In some embodiments, the analysis helps an individual identify when they smirk, are condescending, trivialize another's experience, or exhibit some other behavior the individual desires to modify or eliminate. In some cases, the game can be a game of chance such as poker. The mental state analysis can allow a computer or another player to predict the type of poker hand an individual has, for example.

The flow 100 can include inferring mental states 132 with regard to the game based on the mental state data which was collected. The inferred mental states can include one or more of frustration, confusion, disappointment, hesitation, cognitive overload, focusing, engagement, attention, boredom, exploration, confidence, trust, delight, disgust, skepticism, doubt, satisfaction, excitement, laughter, calmness, stress, and curiosity. The inferring of mental states can be performed for an individual or for a plurality of people who are playing the game.

The flow 100 continues with modifying the game based on the mental state information 140. The game can be modified in numerous ways, methods with which those of skill in the art will be familiar. The modifying the game can include modifying an avatar that represents the individual. The avatar can be selected by the individual. Alternatively, the avatar can be selected by the game based, at least in part, on the mental states of the individual. The avatar can be animated based on the mental state information. For example, if the individual is excited, the avatar can move around the game in an excited fashion. In some embodiments, the modifying the game can include modifying an avatar that represents a group of people who are playing the multiplayer game. The avatar can represent a collective mental state for the group of people.

The modifying the game can be based on analysis including facial analysis. Facial analysis can be performed for an individual or for a group of people who are playing a multiplayer game. The facial analysis can be based on collecting facial data where the facial data can include facial regions. The facial analysis can be based on collecting facial data where the facial data can include facial landmarks. The facial data including the facial landmarks can be used to evaluate mental states. The facial analysis that can be based on facial landmarks can be used to change or modify an avatar, where the avatar can represent the individual. The changing or modifying the avatar can include size, shape, color, texture, pattern, movement, and so on, of the avatar. The modifying the avatar that represents the individual can be based on the mental states of the individual. The modifying the avatar can include modifying the face on the avatar. The face on the avatar can be modified to show eye positions, nose location, mouth location, ear locations, etc. The modifying the avatar can include modifying a facial expression of the avatar. In embodiments, the face on the avatar can be modified to show a smile based on a happy mental state of the individual. Similarly, the face on the avatar can be modified to show a frown, a smirk, a wink, a scowl, and so on. The modifying the avatar can include having the face of the avatar mimic the face of the individual involved in the game. The modifying the face of the avatar to mimic the face of the individual can include having the face of the avatar smile, frown, smirk, wink, scowl, blink, laugh, etc., as the individual does so. The modifying the avatar can include having portions of the face of the avatar track landmarks of a face of the individual while the individual is involved in a game. The portions of the face of the avatar can be made to translate, rotate, scale, and so on as landmarks of the face of the individual themselves translate, rotate, scale, etc.

The facial landmarks that can be included in the facial data and on which facial analysis can be based can include eyebrows, eyes, corners of eyes, a nose, a mouth, corners of a mouth, ears, and so on. The facial data can be analyzed to identify facial action units such as facial action units included in the facial action coding system (FACS). One or more facial action units can be identified. The facial action units can include inner brow raiser (AU1), upper lip raiser (AU5), nose wrinkler (AU9), and so on. The facial action units can be used to identify facial expressions, where the facial expressions can include a smile, a frown, a smirk, etc. The facial expressions, the facial analysis, and so on can be used to identify mental state information.

The mental state information that can be identified can be used to change or modify an avatar so that the avatar can mimic the mood of a player while the individual is involved in a game. The mood of the individual that can be mimicked by the avatar can include happy, sad, angry, stressed, bored, and so on. In embodiments, if the individual is smiling, then the avatar can be changed to show a smile, to behave in a happy manner, and so on. As the facial data of the individual changes, so too can the avatar change to reflect the change in facial data of the individual. The facial data of the individual can include facial landmarks, as discussed above. In a similar manner, the body of the avatar can be changed or modified to mimic the mood of the player. Continuing with the smile example, the avatar can be modified to show laughter, to shake with laughter, to dance about, etc. The modifying of the face of the avatar can be based on facial data including facial landmarks of the individual. As the facial landmarks of the individual change, the similar features on the avatar corresponding to the facial landmarks can also be made to change. In some cases, the use of normal mapping is utilized in the process of mimicking facial expressions.

The modifying the game can include changing tasks with which the individual is presented. Many games include a sequence of challenges which must be overcome as the player progresses through the game. The type of challenge or task can be modified based on the mental states of the individual. The changing tasks can include making the game harder. The making the game harder may be based on the mental state information including an indication of boredom. In some embodiments, changing tasks include making the game easier. The making the game easier can be based on the mental state information including an indication of frustration.

The game can be a multiplayer game. The multiple people in the game can be together in one room, as is often the case with a party game. Alternatively, the multiple people can be connected through a network such as the Internet. The modifying the game can include changing tasks presented in the multiplayer game. The sequence of challenges can be modified in order and/or in character. In the case of a dance game, the types of dance and music can be modified. The modifying can include changing roles within a team. With multiple players, differing roles might be needed for the multiple players who make up the team. In one example, a person who is more confident can be selected to be a team leader. In another example, a person who is calmer can be chosen to be the collector of the supplies. The modifying can include grouping the individual with others based on the mental state of the individual. When a multiplayer team has two or more teams that play against each other, such as in a sporting or military type game, the grouping of sides can be modified. For example, a mix of confident and nervous people can be combined on each team so that both experienced and new players are shared between teams. The modifying the game can include changing a role for the individual. For example, when an individual starts to exhibit mental states associated with tedium, their role can be changed within the game. The modifying the game can include advancing the individual through game levels. For example, when a person exhibits unusual confidence they might be allowed to skip levels within a game to move them to more challenging game scenarios.

In some games, an individual plays against or with a computer generated player. The flow 100 can include developing a mental state for a CPU or computer generated player 150. The computer generated player can compete against the individual. The computer generated player can be on a team with the individual. The computer generated player can respond to the individual's affect. For example, the computer generated player might inject a more engaging persona to enliven the game when a person starts to slow down or evidence an affect that reflects being tired, bored, or disinterested.

The game can be a party game. The party game can be modified to develop a communal mental state where the mental state of the individual is aggregated within the community mental state. For example, a special event can be offered if a certain number of people achieve a certain state of excitement. For instance, if a group of gamers all smile at the same time then a new game level might be released for the next 24 hours free of charge.

In some embodiments, flow 100 includes displaying the mental state information 160 in a visualization. The visualization can be a graphical or textual presentation of the mental state information. The visualization can be used within a social network to easily grasp how the individual is reacting to the gaming environment. Alternatively, the visualization can be used by game developers or market researchers to better understand the individual's reaction to the game or a portion thereof. Optimal product placement and advertisements could be included based on the visualization. Various steps in the flow 100 may be changed in order, repeated, omitted, or the like without departing from the disclosed inventive concepts. Various embodiments of the flow 100 may include a computer program product embodied in a non-transitory computer readable medium that includes code executable by one or more processors.

Figure 2:
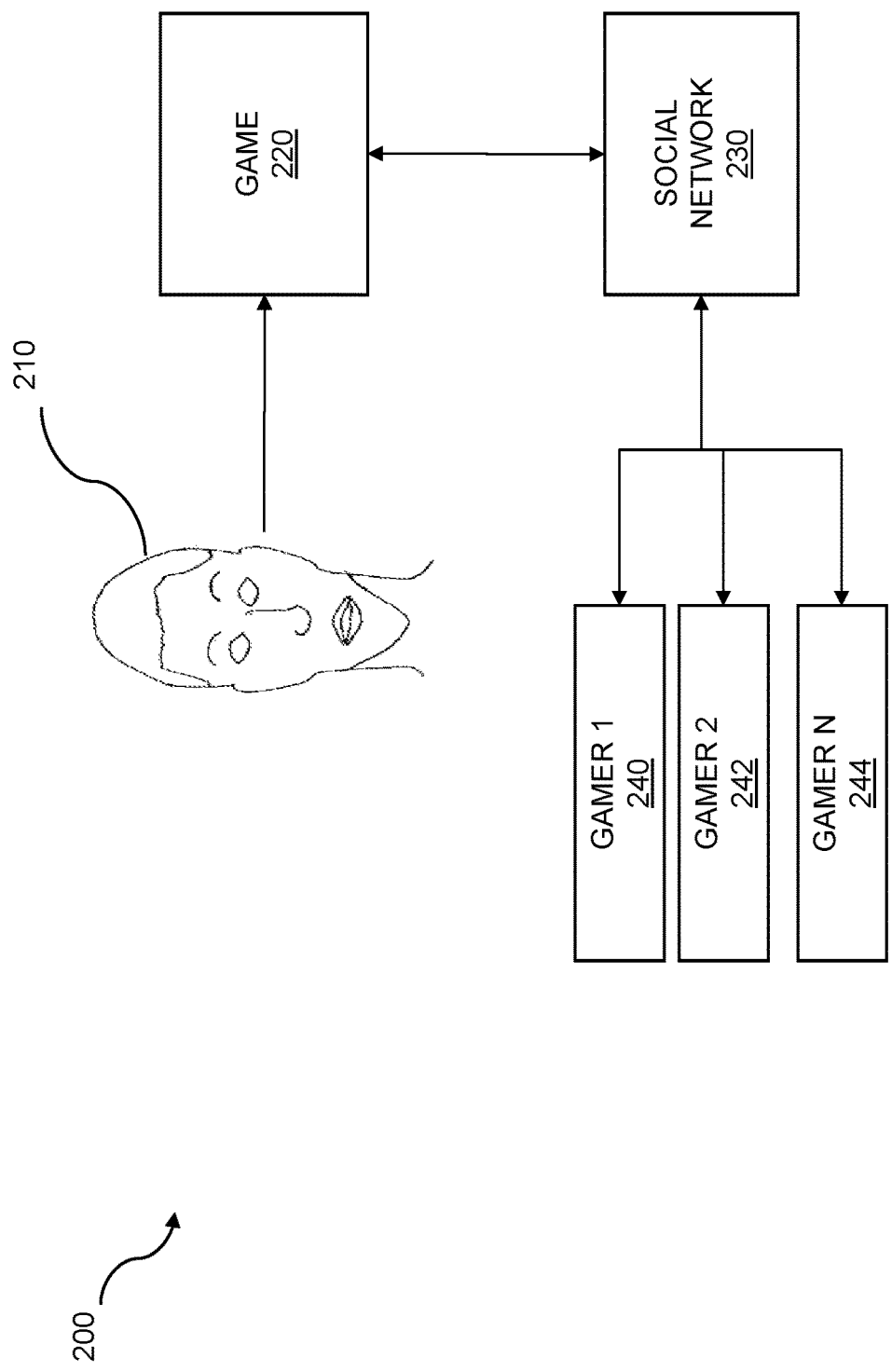
FIG. 2 is a diagram showing social network/gaming interaction.

FIG. 2 is a diagram showing social network/gaming interaction. In the diagram 200, a person 210 is shown interacting with a game 220. The game 220 can be a computer game, a video game, a personal game, a kinetic game, or the like. A kinetic game can be considered a motion-oriented game such as the Nintendo Wii™, Microsoft Kinect™, Sony PlayStation Move™. The person 210 can interact with the game using a keyboard, a mouse, a joystick, a game controller, a game remote, a motion sensor, a camera sensor, or some other device. As the person 210 interacts with the game 220, the mental states of the person 210 can be observed and/or analyzed. The mental states of the person can be captured based on a webcam, a video camera, or another camera device. Facial data obtained from a webcam can include facial actions and head gestures which can in turn be used to infer mental states. The mental states can also be captured using a biosensor. The biosensor can capture information on electrodermal activity (EDA) or skin conductance or galvanic skin response (GSR), accelerometer readings, skin temperature, heart rate, heart rate variability, and other types of physiological analysis of an individual. The video and physiological observations can be performed and analyzed locally. Alternatively, the video and physiological observations can be captured locally on a client machine with analysis being performed on a remote server machine.

Information on the game 220 along with mental state information on the person 210 can be communicated to a gaming server or to a social network 230. The social network 230 can be Facebook™, Myspace™, Steam™, Twitter™, or another social structure. The social structure can be made up of nodes, where each node represents an individual or organization, and where various nodes have an interdependency such that communication is possible between various nodes. The social network 230 can comprise a gaming community. Affect, based on camera or on physiological observations, is communicated to the social network 230. Other individuals who are part of the social network 230 can participate in the game 220. For example, gamer 1 240, gamer 2 242, through gamer N 244 can be part of the game 220 that the person 210 is playing. In some embodiments, the gamers are considered to be a clan. The mental states of the person 210 can be presented to the other gamers. Likewise, the mental states of the other gamers can be presented to the person 210. The mental state of the person 210 can be presented to the other gamers who are part of the social network 230 through an avatar representation, through a set of color representations, or through a graphical representation. Likewise, the mental state information can be represented in one of a group selected from a bar graph, a line graph, a smiling face, a frowning face, and a text format or the like. In some embodiments, affect is communicated to the social network 230.

Communication of affect can be accomplished in real time while the game 220 is being played. In some embodiments, the game 220 is modified based on this real time affect communication. Alternatively, communication of affect can be after the game 220 is completed or after a specific session or goal of the game 220 is completed. The affect can be communicated as a single graphical representation such as a graph, an avatar, or a smiley face. The graphical representation could be a set of stars, hearts, or another symbol that can connote positive or negative rating. The affect can be communicated numerically, with the number indicating a positive or negative experience with the game 220 or a portion of the game. A set of thumbnails can be displayed where the thumbnails are snapshots of the game 220 as it is played. Another set of thumbnails can be displayed of facial expressions from the person 210 as he or she interacts with the game 220.

In some embodiments, affect is communicated to the social network 230 where some or all of the people are not gamers playing the game 220. The people on the social network 230 might want to know what activities the person 210 is involved with, including such activities as the game 220, and the reaction of the person 210 to the activities. The reaction can include the affect of the person 210. The person's reaction to the game 210 can be used to recommend the game 210 or a part of the game to others on the social network 230.

It will be understood that throughout this disclosure, while a reference may be made to an individual or a person with respect to the gaming, mental state collection, analysis, sharing, and the like, the concepts apply equally to groups of people playing games. The people may be in the same room or may be remote from one another playing across a network such as the Internet. All such embodiments for both groups and individuals fall within the scope of this disclosure.

Figure 3:
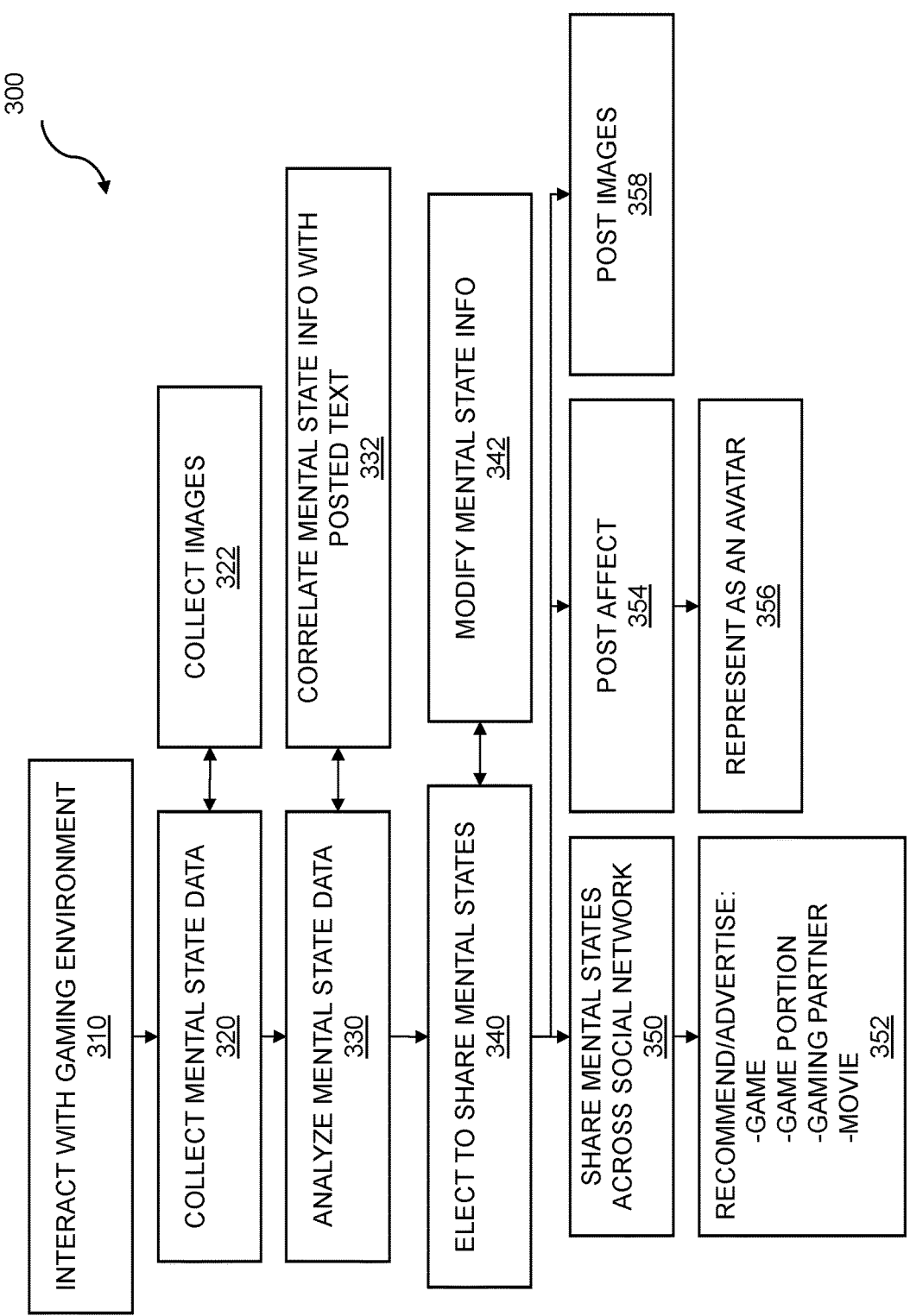
FIG. 3 is a flow diagram showing social network interaction with gaming.

FIG. 3 is a flow diagram showing social network interaction with gaming. A flow 300 describes a computer implemented method for gaming. The flow 300 begins with an individual interacting with a gaming environment 310. The gaming environment can include a computer game, a video game, a personal game, a kinetic game, or the like. The flow 300 continues with collecting mental state data 320 of the individual while the individual is involved in the gaming environment. The mental state data can be based on facial expressions and physiological data. The mental state data can include collecting action units. Alternatively, mental state data can involve collecting facial expressions, such as smiles or brow furrows. Physiological data can be obtained from video observations of a person. For example, heart rate, heart rate variability, autonomic activity, respiration, and perspiration can be observed from video capture. Alternatively, in some embodiments, a biosensor is used to capture physiological information and is also used to capture accelerometer readings. The flow 300 continues with analyzing the mental state data 330 to produce mental state information. In some embodiments, mental state data collection and mental state analysis are performed in a single step. Additionally, in some embodiments, the analyzing of the mental state information occurs along with posted text to correlate the mental state information with the posted text 332. Posted text can take the form of text input for a game, blog entries, Twitter™ comments, and the like. When the mental state data is analyzed, the game can be modified based on the individual's affect. For instance, music played along with the game could be modified based on the heart rate of the individual. The music tempo and volume could each be increased if a person starts to become disinterested. In another example, the pace of the game could be modulated based on the engagement or activation of the gamer. Likewise, a scene within the game could be modified to help calm a person that is becoming agitated.

The analyzing of mental state data can include inferring of mental states for the individual as they interact with the gaming environment 310. The analyzing can be performed locally on a client computer system. The analyzing can be performed on a server computer or another remote system.

The flow 300 continues with sharing the mental state information across a social network 350. The social network can comprise a gaming community. People on the social network who receive the mental state information can themselves be gamers. In some cases, however, the people on the social network who receive the mental state information might only be participants in the social network and not gamers themselves, or at least not involved with the game with which the individual is interacting, and thus might only be interested in the individual and any activities or reactions of the individual. The sharing of mental states could replace or augment other rating systems. For example, other rating systems include selecting whether the individual liked, disliked, loved, etc. a game or video. The affect for the person could be used to augment such a rating system. Alternatively, the person's affect could replace and be used as the only rating system for games, videos, and the like. In some embodiments, an affect is shared across a network which indicates the level of engagement or excitement for the individual. In a music game, for example, the people on the social network could see the excitement of the individual or the band made up of individuals when they play certain music or musical instruments. In some embodiments, mental state information is shared across a social network based on the mental states. Using the expression of smiles or laughter, for example, by an individual or group of people, mental state information can be propagated across a social network. In embodiments based on smiles and laughter, mental state information is propagated by text messaging or Twitter™ to those in a select group. Based on this information, others can choose to join in the gaming environment.

In some embodiments, the flow 300 includes a step, before the sharing of mental states 350, of electing, by the individual, to share the mental state information 340. For example, an individual can opt in to sharing of mental states in general, only for a particular game, or only for a specific session. In some embodiments, the individual elects to share the mental state information after a session is completed. In other embodiments, the sharing is in real time so that the gaming experience and reactions are modified real time as the individual is participating in the game. In some embodiments, when a person elects to share mental states, the mental state information is modified 342. For example, a person can choose to share a mental state which is more confident, happier, or positive at certain times than the inferred mental states which were analyzed. In some cases, the flow 300 includes handicapping the affect or mental state. This handicapping can equalize opportunities for a game where participants are both more and less experienced.

In some embodiments, the flow 300 includes posting affect 354 from the individual to others who are involved in the gaming environment. The posting of affect can be represented through a set of color representations, through a graphical representation, through a set of thumbnails, or through a text communication. The posting of affect can include representation by an avatar 356. The avatar can be static, such as simply showing a smile, or the avatar can be animated to show excitement or even activity related to the game in which the individual is participating.

In some embodiments, the flow 300 includes collecting images 322 of the individual while the individual is involved in the gaming environment. These images can be video or can be individual still photographic images. The images can be standard visual light photographs or can include infrared or ultraviolet images. In some embodiments, the flow 300 includes posting an image 358 from a session within the gaming environment. The image can include a facial expression. A group of images can be included as a set of thumbnails. A facial expression can be selected because it is an animated expression. A facial expression can be selected because it is an unusual facial expression. A facial expression can be selected because it is a typical facial expression. In some embodiments, the image posted includes a video of the whole person or face. The images posted can share the highlights of the game being played.

Based on the mental states of the individual, recommendations 352 to or from the individual can be provided. The flow 300 can include recommending a game, based on the mental state information, to others in the social network. A recommendation can include recommending part of a game, based on the mental state information, to others in the social network.

A recommendation can include recommending a gaming partner based on the mental state information. A gaming partner can be recommended based on skill, role, compatibility, or coaching ability. A correlation can be made between an individual and other individuals within the social network to identify those types of gaming partners most preferred. Based on the correlation and the mental states of the individual, a gaming partner can be recommended.

One or more recommendations can be made to the individual based on the mental states of the individual. A game or portion of a game can be recommended to the individual based on his or her mental states as they interact with the game. A correlation can be made between the individual and others with similar affect exhibited during the game. The correlation can include a record of other games or other experiences along with their affect. Likewise, a movie, video, video clip, webisode or another activity can be made to individual based on their affect.

The flow 300 can include advertising a game based on the mental state information. An advertisement can be made to the individual because the individual had positive mental states for a certain game, and therefore another game is expected to evoke similar positive mental states. An advertisement can be made to the individual because the individual had negative mental states for a certain game, and therefore a different game is expected to evoke a more positive group of mental states. Based on mental state correlations with other people in the gaming environment an advertisement can be tailored for the individual.

The flow 300 can include recommending a movie, video, video clip, game, or portion of a game based on the mental state information from the gaming environment. When an individual has a positive set of mental states with a specific gaming experience, a similar movie, television show, web series, webisode, video clip, book, magazine, or other media may be recommended. Various steps in the flow 300 may be changed in order, repeated, omitted, or the like without departing from the disclosed inventive concepts. Various embodiments of the flow 300 may include a computer program product embodied in a non-transitory computer readable medium that includes code executable by one or more processors.

Figure 4:
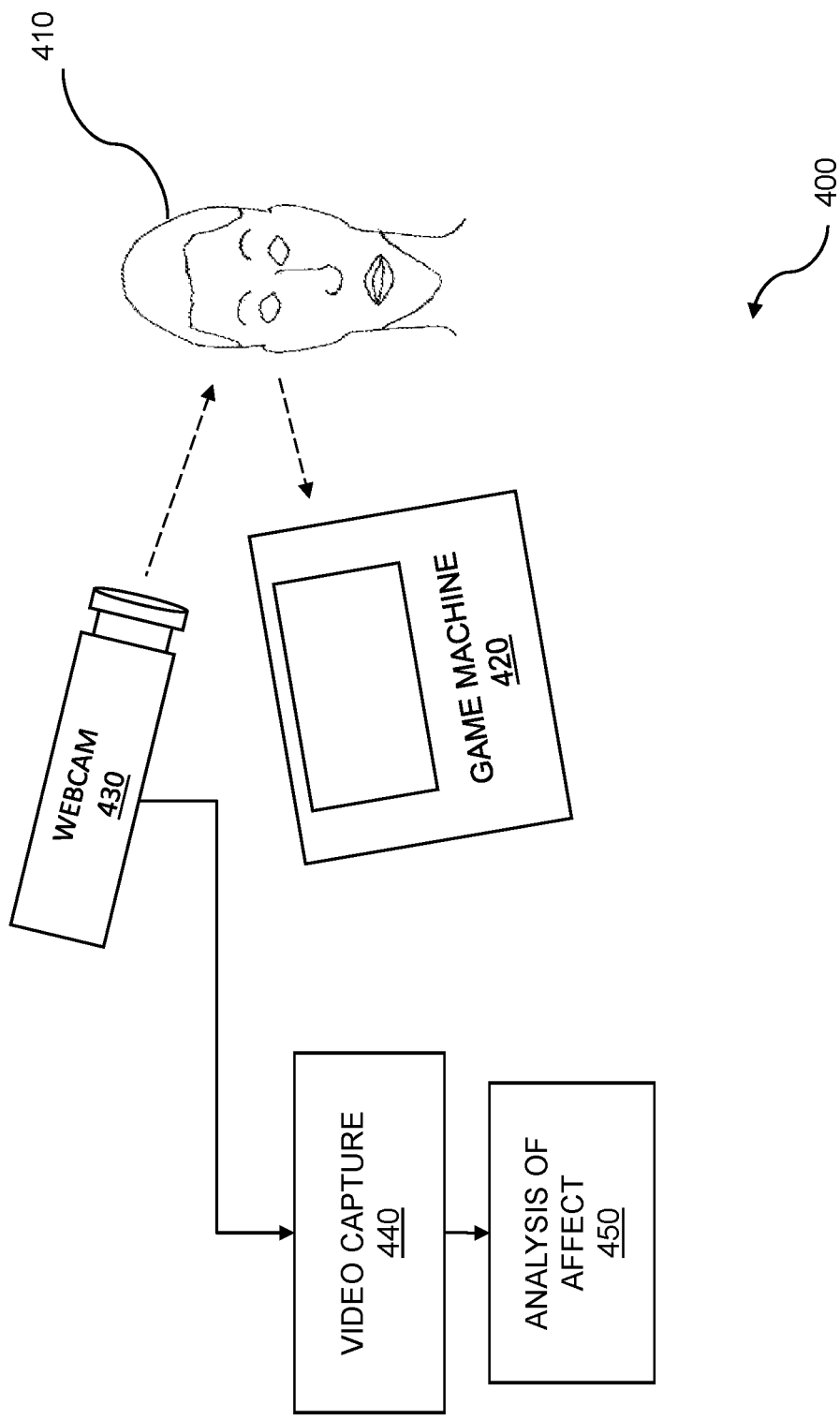
FIG. 4 is a diagram showing image capture during gaming.

FIG. 4 is a diagram showing image capture during gaming. A system 400 includes a game machine 420 and a webcam 430. The system 400 captures facial response to a rendering on the game machine 420 and the experience with the game, wherein the game can be within an electronic gaming environment. The facial data can include video and collection of information relating to mental states. In some embodiments, the webcam 430 captures video of a person 410. The webcam, as the term is used herein and in the claims, can be a video camera, still camera, thermal imager, CCD device, phone camera, three-dimensional camera, a depth camera, multiple webcams used to show different views of a person, or any other type of image capture apparatus that allows captured data to be used in an electronic system.

The game machine 420 can show a rendering relating to gaming action. The game machine can include any electronic display, including but not limited to, a computer display, a laptop screen, a net-book screen, a tablet computer screen, a cell phone display, a mobile device display, a remote with a display, a television, a projector, or the like. The game machine can also include a keyboard, mouse, joystick, touchpad, wand, motion sensor, and another input means. The game can be from a webpage, a website, a web-enabled application, a virtual world, or the like. The images of the person 410 can be captured by a video capture unit 440. In some embodiments, video is captured, while in others, a series of still images are captured. In embodiments, a webcam is used to capture the facial data.

Analysis of action units, gestures, and mental states can be accomplished using the captured images of the person 410. The action units can be used to identify smiles, frowns, and other facial indicators of mental states. The gestures, including head gestures, can indicate interest or curiosity. For example, a head gesture of moving toward the gaming machine 420 can indicate increased interest or a desire for clarification. Based on the captured images, analysis of physiology can be performed. Analysis of affect 450 can be performed based on the information and images which are captured. The analysis can include facial analysis and analysis of head gestures. The analysis can include analysis of physiology including heart rate, heart variability, respiration, perspiration, temperature, and other bodily evaluation.

Figure 5:
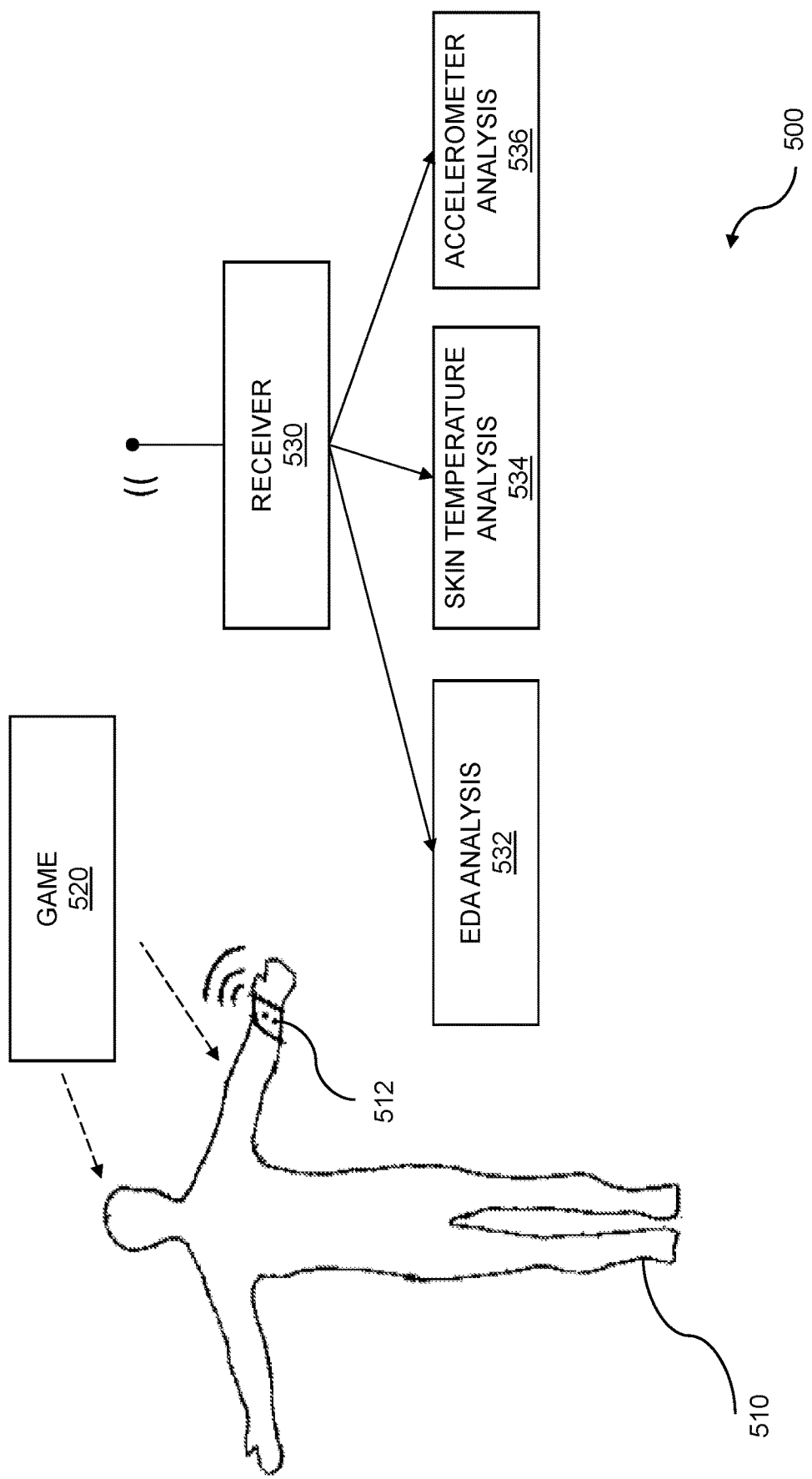
FIG. 5 is a diagram showing sensing and interaction with gaming.

FIG. 5 is a diagram showing sensing and interaction with gaming. A system 500 can analyze a person 510, for whom data is being collected, as the person 510 interacts with a game 520. The game 520 can be a video game, a computer game, a group party game, an educational game, a kinetic game, or another game. In the system 500, the person 510 has a sensor 512 attached to him or her. The sensor 512 can be placed on the wrist, palm, hand, head, or another part of the body. The sensor 512 can include detectors for electrodermal activity, skin temperature, and accelerometer readings. Other detectors can be included as well, such as heart rate, blood pressure, EKG, EEG, further brain waves, and other physiological detectors. The sensor 512 can transmit information collected to a receiver 530 using wireless technology such as Wi-Fi, Bluetooth, 802.11, cellular, or other bands. The receiver can provide the data to one or more components in the system 500. In some embodiments, the sensor 512 records various physiological information in memory for later download and analysis. In some embodiments, the download of data is accomplished through a USB port.

In some embodiments, electrodermal activity is collected, sometimes continuously, every second, four times per second, eight times per second, 32 times per second, or on some other periodic basis as the person 510 interacts with the game 520. In some embodiments, aperiodic sampling is performed using a Boltzmann distribution or in a lumpy fashion based on events of interest. The electrodermal activity can be recorded. The recording can be to a disk, a tape, onto flash memory, into a computer system, or streamed to a server. The electrodermal activity can be analyzed 532 to indicate arousal, excitement, boredom, or other mental states based on changes in skin conductance. Skin temperature can be collected on a periodic basis or an as needed basis and then recorded. The skin temperature can be analyzed 534 and, based on temperature changes, can indicate arousal, excitement, boredom, or other mental states.

Accelerometer data can be collected and can indicate one, two, or three dimensions of motion. The accelerometer data can be recorded. The accelerometer data can be analyzed 536 and can indicate gaming activities, motions, and involvement based on accelerometer data.

In some embodiments, multiple sensors 512 are attached to an individual. In embodiments, the sensors are incorporated in sweat bands that a person wears. For instance, a sensor can be attached to each wrist and each ankle to detect motions and relative positions of the arms and legs. A sensor can also be attached to the head or elsewhere on the body. In embodiments, the sensor is used to evaluate motions for certain sporting types of games, such as soccer, bowling, or boxing. In embodiments, the sensors are used to evaluate positions in yoga, and are then used to have the game help the gamer learn better body position. Further, sensors can be used to evaluate both motion and emotion. For instance, a golf swing can be evaluated along with whether or not the gamer was calm during the swing.

Figure 6:
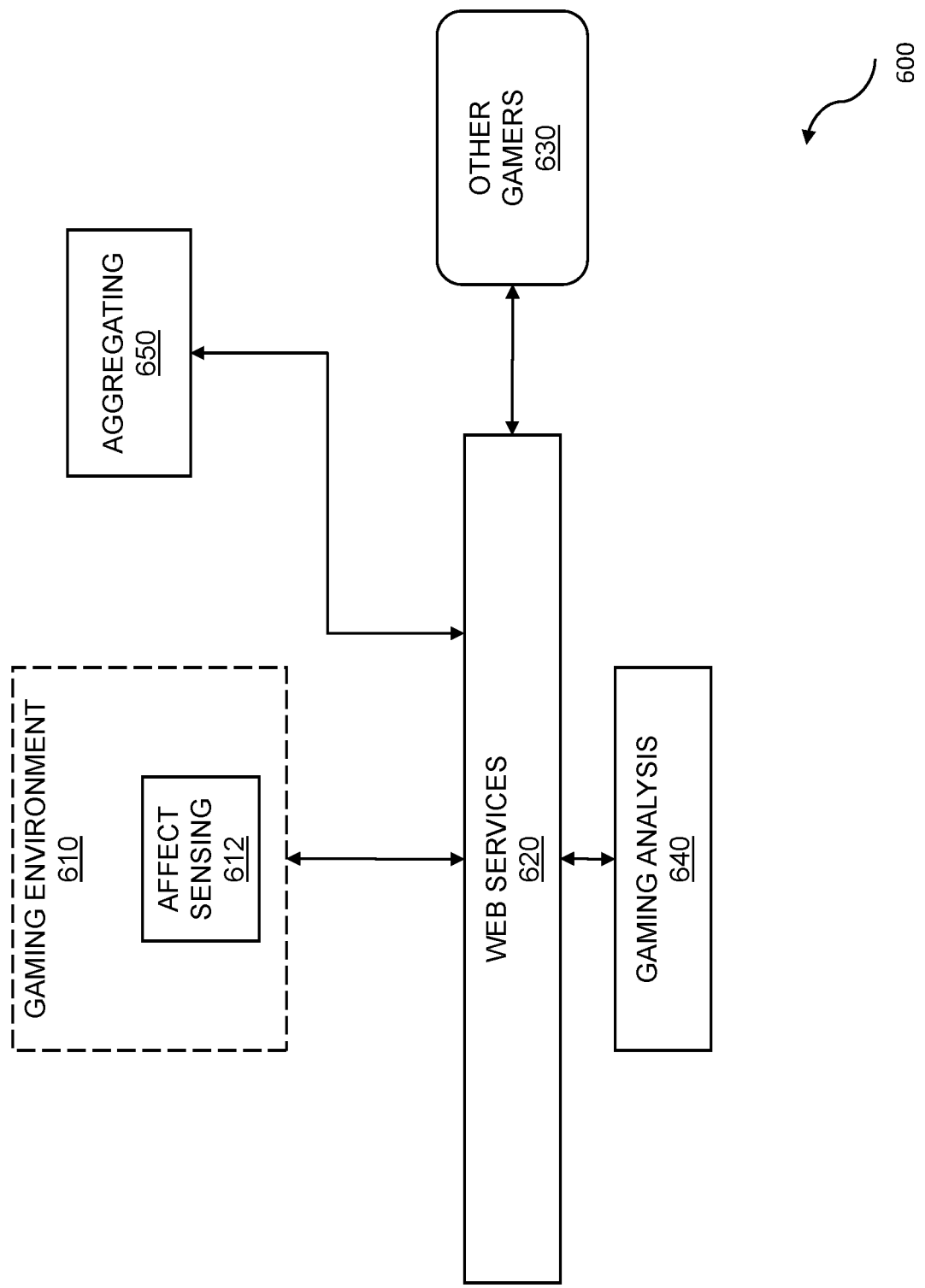
FIG. 6 is a diagram showing web services gaming analysis.

FIG. 6 is a diagram showing web services gaming analysis. The system 600 includes a gaming environment 610 and web services 620. The gaming environment can be supported by a computer game, a video game, a personal game, a kinetic game, or the like. The gaming environment 610 can include affect sensing 612 apparatus for a gamer. The affect sensing 612 can include collecting one or more of facial, physiological, and accelerometer data. The physiological data analysis can include electrodermal activity or skin conductance, skin temperature, heart rate, heart rate variability, respiration, and other types of analysis of a human being. The gaming environment 610 can include the needed hardware for performing the affect sensing. In other embodiments, there is a separate device such as a laptop, personal computer, or mobile device which captures data associated with the affect sensing 612. The output of the affect sensing 612 can be forwarded for analysis to the web services 620. The web services 620 can be part of a gaming system. Alternatively, the web services 620 can be a separate analysis system which provides input to the gaming system. The web services 620 can be a server or can be a distributed network of computers.

In some embodiments, some analysis is performed by the affect sensing 612 apparatus. In other embodiments, the affect sensing 612 apparatus collects data and the analysis is performed by the web services 620. In embodiments, other gamers 630 are playing the game along with the gamer who is having his or her affect sensed. In embodiments, each of the gamer and the other gamers 630 have their affect sensed and provided to the web services 620.

Analysis of the affect in the gaming environment is performed by the gaming analysis 640 module. The gaming analysis 640 module can be part of the gaming system, part of the web services 620, or part of a computer system that provides an analysis engine. The facial, physiological, and accelerometer data can be analyzed along with the gaming context. Based on this analysis, the game can be modified in various ways, as previously described. The game can be modified based on a single gamer whose affect has been sensed. An aggregating 650 engine can analyze the sensed affect from the gamer and the other gamers. The aggregating 650 engine can be used to modify the game based on the combined affect sensed from all of the gamers involved. In some embodiments, the aggregating 650 engine gathers other sources of information for aggregation including news feeds, Facebook™ pages, Twitter™, Flickr™, and other social networking and media. The social networking pages related to the gamers can be analyzed during the aggregating. In some embodiments, the game is modified based on the aggregation of mental state information as well as other social information.

Figure 7:
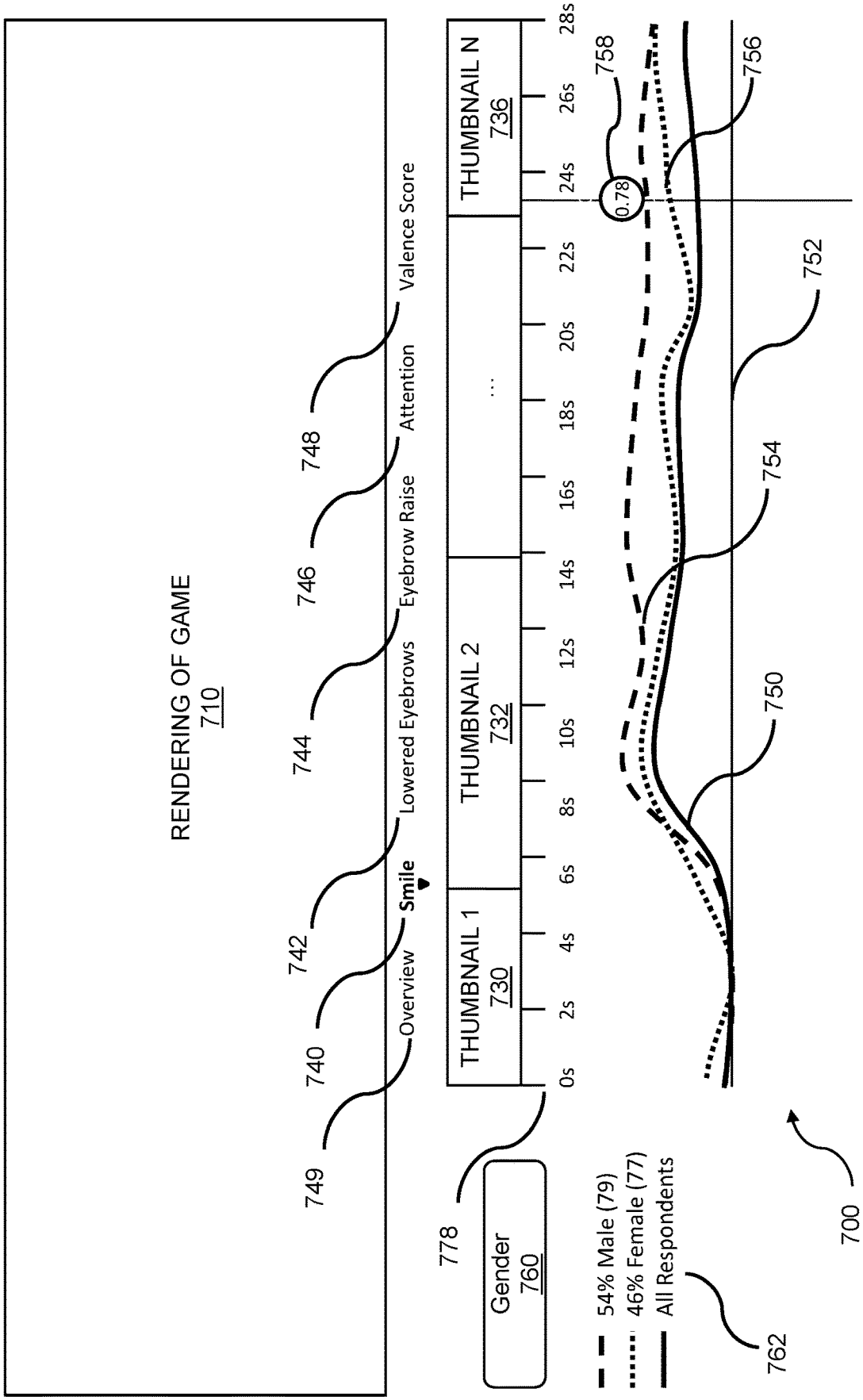
FIG. 7 is a graphical representation of mental state analysis.

FIG. 7 is a graphical representation of mental state analysis that can be shown for gaming analysis and can be presented on an electronic display. The gaming analysis can be used to modify the game and can be used to improve game play. The display can be a television monitor, projector, computer monitor (including a laptop screen, a tablet screen, a net-book screen, and the like), a cell phone display, a mobile device, or another electronic display. An example window 700 is shown which includes a rendering of a game 710 along with associated mental state information. The visualization can further comprise the rendering related to the game 710. A user can select among a plurality of game renderings using various buttons and/or tabs. The user interface allows a plurality of parameters to be displayed as a function of time, synchronized to the game rendering 710. Various embodiments have any number of selections available for the user, and some are other types of renderings instead of video. A set of thumbnail images for the selected rendering, such as Thumbnail 1 730, Thumbnail 2 732, through Thumbnail N 736, can be shown below the rendering along with a timeline 778. The thumbnails can show a graphic "storyboard" of the game rendering. The storyboard can assist a user in identifying a particular scene or location within the game rendering. Some embodiments do not include thumbnails, or have a single thumbnail associated with the rendering, while various other embodiments have thumbnails of equal length, while others have thumbnails of differing lengths. In some embodiments, the start and/or end of the thumbnails are determined based on changes in the captured gamer mental states associated with the rendering, or are based on particular points of interest in the game rendering. Thumbnails showing one or more gamers can be shown along the timeline 778. The thumbnails of gamers can include peak expressions, expressions at key points in the game rendering 710, etc.

Some embodiments include the ability for a user to select a particular type of mental state information for display using various buttons or other selection methods. The mental state information can be based on one or more descriptors. The one or more descriptors can include, but are not limited to, one of AU4, AU12 and valence. By way of example, in the window 700, the smile mental state information is shown as the user could have previously selected the Smile button 740. Other types of mental state information that can be available for user selection in various embodiments include the Lowered Eyebrows button 742, Eyebrow Raise button 744, Attention button 746, Valence Score button 748, or other types of mental state information, depending on the embodiment. An Overview button 749 can be available to allow a user to show graphs of the multiple types of mental state information simultaneously. The mental state information can include probability information for one or more descriptors, and the probabilities for the one of the one or more descriptors can vary for portions of the game rendering.

Because the Smile option 740 has been selected in the example shown, smile graph 750 can be shown against a baseline 752, showing the aggregated smile mental state information of the plurality of individuals from whom mental state data was collected for the game. The male smile graph 754 and the female smile graph 756 can be shown so that the visual representation displays the aggregated mental state information. The mental state information can be based on a demographic basis as those gamers who comprise that demographic react to the game. The various demographic based graphs can be indicated using various line types as shown or can be indicated using color or another method of differentiation. A slider 758 can allow a user to select a particular time of the timeline and show the value of the chosen mental state for that particular time.

In some embodiments, various types of demographic-based mental state information are selected using the demographic button 760. Such demographics can include gender, age, race, income level, education, or any other type of demographic, including dividing the respondents into those respondents that had higher reactions from those with lower reactions. A graph legend 762 can be displayed indicating the various demographic groups, the line type or color for each group, the percentage of total respondents and/or absolute number of respondents for each group, and/or other information about the demographic groups. The mental state information can be aggregated according to the demographic type selected. Thus, aggregation of the mental state information is performed on a demographic basis so that mental state information is grouped based on the demographic basis, for some embodiments. A product or service developer could be interested in observing the mental state of a particular demographic group and the mental state information for such a group could be usefully aggregated.

Figure 8:
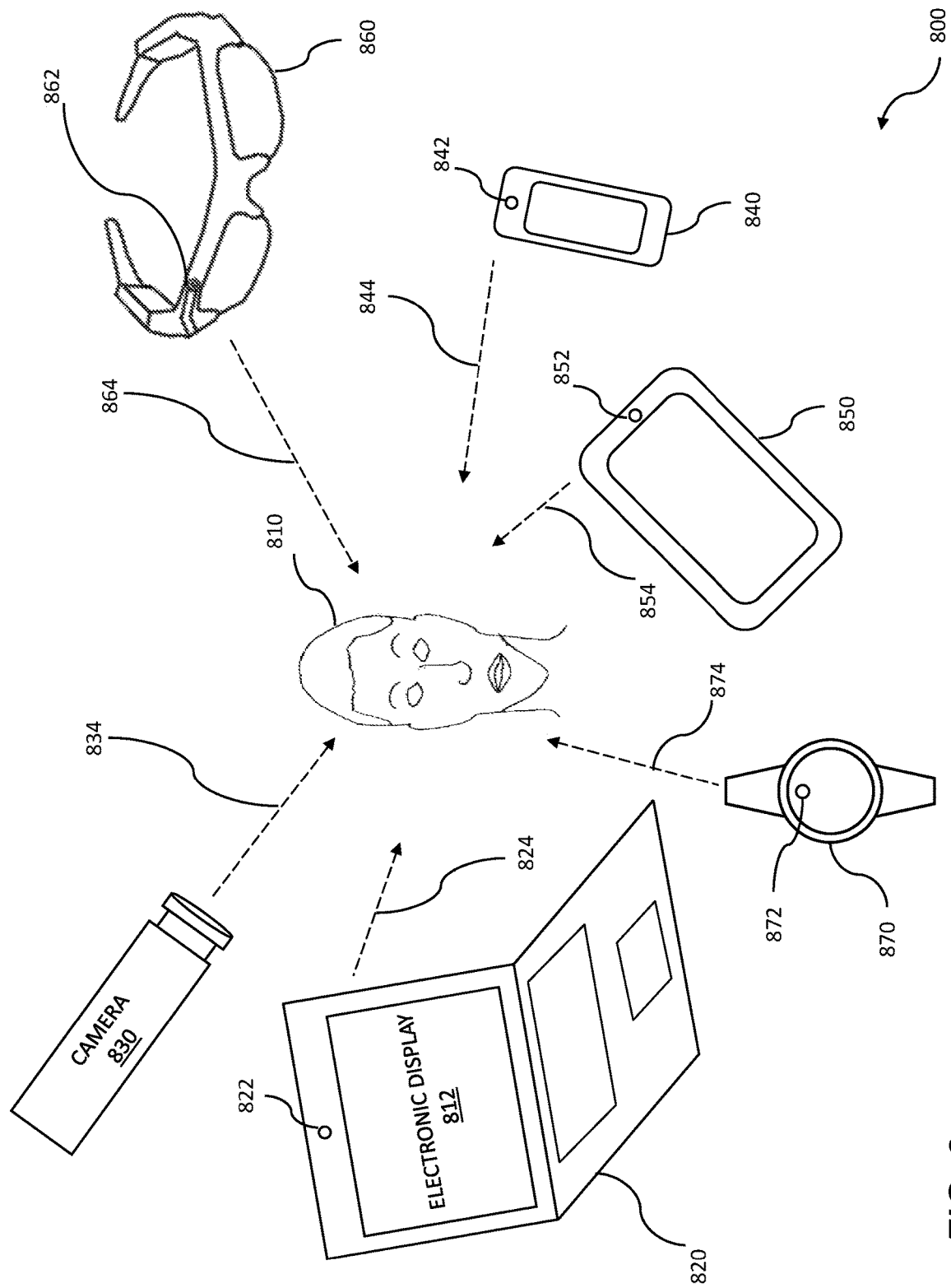
FIG. 8 is a diagram showing image collection including multiple mobile devices.

FIG. 8 is a diagram showing image collection including multiple mobile devices. The images can be collected for evaluating mental states. The evaluating of mental states can be based on using affect within a gaming context. The mental states of multiple people can be evaluated as they interact with a gaming environment. The collected images can be evaluated for an individual to be within a sub-sectional component of a population. The sub-sectional components can be used with performing the evaluation of content of the face. The sub-sectional components can be used to provide a context. In the diagram 800, the multiple mobile devices can be used singly or together to collect video data on a user 810. While one person is shown, the video data can be collected on multiple people. A user 810 can be observed as she or he is performing a task, experiencing an event, viewing a media presentation, and so on. The user 810 can be shown one or more media presentations, political presentations, or social media, or another form of displayed media. The one or more media presentations can be shown to a plurality of people. The media presentations can be displayed on an electronic display 812 or another display. The data collected on the user 810 or on a plurality of users can be in the form of one or more videos, video frames, still images, etc. The plurality of videos can be of people who are experiencing different situations. Some example situations can include the user or plurality of users being exposed to TV programs, movies, video clips, social media, and other such media. The situations could also include exposure to media such as advertisements, political messages, news programs, and so on. Video data can be collected on one or more users in substantially identical or different situations and viewing either a single media presentation or a plurality of presentations. The data collected on the user 810 can be analyzed and viewed for a variety of purposes including expression analysis, mental state analysis, and so on. The electronic display 812 can be on a laptop computer 820 as shown, a tablet computer 850, a cell phone 840, a television, a mobile monitor, or any other type of electronic device. In one embodiment, expression data is collected on a mobile device such as a cell phone 840, a tablet computer 850, a laptop computer 820, or a watch 870. Thus, the multiple sources can include at least one mobile device, such as a phone 840 or a tablet 850, or a wearable device such as a watch 870 or glasses 860. A mobile device can include a forward facing camera and/or a rear-facing camera that can be used to collect expression data. Sources of expression data can include a webcam 822, a phone camera 842, a tablet camera 852, a wearable camera 862, and a mobile camera 830. A wearable camera can comprise various camera devices such as the watch camera 872.

As the user 810 is monitored, the user 810 might move due to the nature of the task, boredom, discomfort, distractions, or for another reason. As the user moves, the camera with a view of the user's face can be changed. Thus, as an example, if the user 810 is looking in a first direction, the line of sight 824 from the webcam 822 is able to observe the user's face, but if the user is looking in a second direction, the line of sight 834 from the mobile camera 830 is able to observe the user's face. Furthermore, in other embodiments, if the user is looking in a third direction, the line of sight 844 from the phone camera 842 is able to observe the user's face, and if the user is looking in a fourth direction, the line of sight 854 from the tablet camera 852 is able to observe the user's face. If the user is looking in a fifth direction, the line of sight 864 from the wearable camera 862, which can be a device such as the glasses 860 shown and can be worn by another user or an observer, is able to observe the user's face. If the user is looking in a sixth direction, the line of sight 874 from the wearable watch-type device 870, with a camera 872 included on the device, is able to observe the user's face. In other embodiments, the wearable device is another device, such as an earpiece with a camera, a helmet or hat with a camera, a clip-on camera attached to clothing, or any other type of wearable device with a camera or another sensor for collecting expression data. The user 810 can also use a wearable device including a camera for gathering contextual information and/or collecting expression data on other users. Because the user 810 can move her or his head, the facial data can be collected intermittently when she or he is looking in a direction of a camera. In some cases, multiple people can be included in the view from one or more cameras, and some embodiments include filtering out faces of one or more other people to determine whether the user 810 is looking toward a camera. All or some of the expression data can be continuously or sporadically available from the various devices and other devices.

The captured video data can include facial expressions and can be analyzed on a computing device such as the video capture device or on another separate device. The analysis can take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capturing device.

Figure 9:
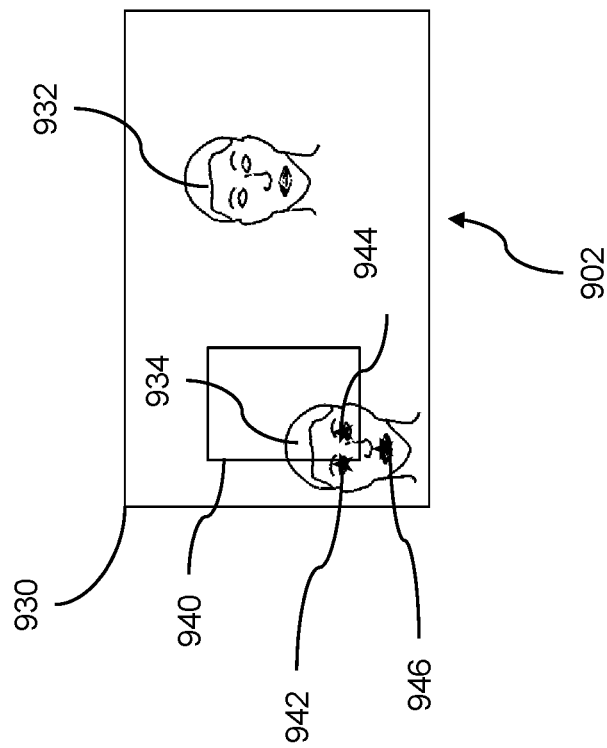
FIG. 9 illustrates feature extraction for multiple faces.
Figure 9:
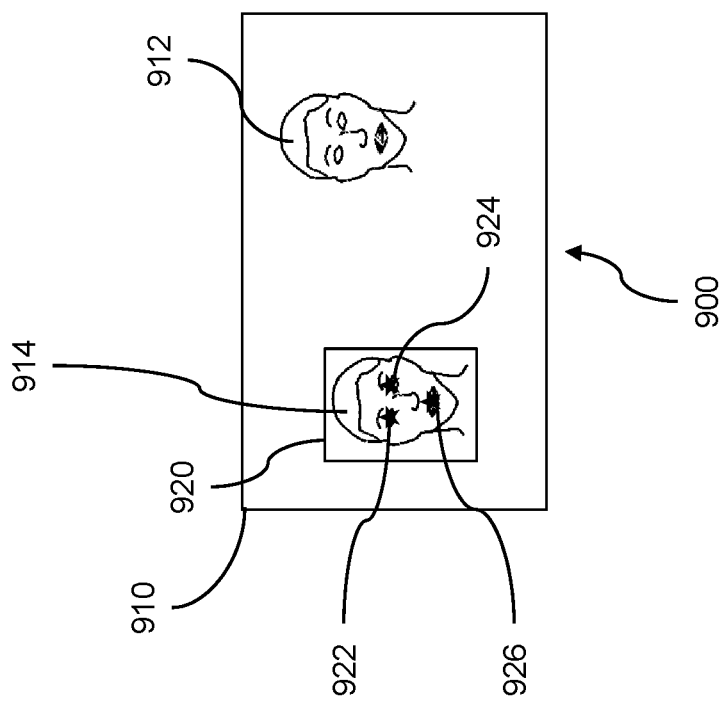

FIG. 9 illustrates facial data collection for multiple faces. The features of multiple faces can be extracted for evaluating mental states. The evaluating of mental states can be based on using affect within a gaming context. The mental states of multiple people can be evaluated as they interact with a gaming environment. The multiple people can be observed through one camera or through multiple cameras, such as one or two cameras per person being observed for mental state data. Features of a face or a plurality of faces can be extracted from collected video data. Feature extraction for multiple faces can be based on sub-sectional components. The sub-sectional components can be used with performing the evaluation of content of the face. The sub-sectional components can be used to provide a context. The feature extraction can be performed by analysis using one or more processors, using one or more video collection devices, and by using a server. The analysis device can be used to perform face detection for a second face, as well as for facial tracking of the first face. One or more videos can be captured, where the videos contain one or more faces. The video or videos that contain the one or more faces can be partitioned into a plurality of frames, and the frames can be analyzed for the detection of the one or more faces. The analysis of the one or more video frames can be based on one or more classifiers. A classifier can be an algorithm, heuristic, function, or piece of code that can be used to identify into which of a set of categories a new or particular observation, sample, datum, etc. should be placed. The decision to place an observation into a category can be based on training the algorithm, by analyzing a known set of data, known as a training set. The training set can include data for which category memberships of the data can be known. The training set can be used as part of a supervised training technique. If a training set is not available, then a clustering technique can be used to group observations into categories. The latter approach, or unsupervised learning, can be based on a measure (i.e. distance) of one or more inherent similarities among the data that is being categorized. When the new observation is received, then the classifier can be used to categorize the new observation. Classifiers can be used for many analysis applications including analysis of one or more faces. The use of classifiers can be the basis of analyzing the one or more faces for gender, ethnicity, and age; for detection of one or more faces in one or more videos; for detection of facial features, for detection of facial landmarks, and so on. The observations can be analyzed based on one or more of a set of quantifiable properties. The properties can be described as features and explanatory variables and can include various data types that can include numerical (integer-valued, real-valued), ordinal, categorical, and so on. Some classifiers can be based on a comparison between an observation and prior observations, as well as based on functions such as a similarity function, a distance function, and so on.

Classification can be based on various types of algorithms, heuristics, codes, procedures, statistics, and so on. Many techniques exist for performing classification. This classification of one or more observations into one or more groups can be based on distributions of the data values, probabilities, and so on. Classifiers can be binary, multiclass, linear, and so on. Algorithms for classification can be implemented using a variety of techniques, including neural networks, kernel estimation, support vector machines, use of quadratic surfaces, and so on. Classification can be used in many application areas such as computer vision, speech and handwriting recognition, and so on. Classification can be used for biometric identification of one or more people in one or more frames of one or more videos.

Returning to FIG. 9, the detection of the first face, the second face, and multiple faces can include identifying facial landmarks, generating a bounding box, and prediction of a bounding box and landmarks for a next frame, where the next frame can be one of a plurality of frames of a video containing faces. A first video frame 900 includes a frame boundary 910, a first face 912, and a second face 914. The video frame 900 also includes a bounding box 920. Facial landmarks can be generated for the first face 912. Face detection can be performed to initialize a second set of locations for a second set of facial landmarks for a second face within the video. Facial landmarks in the video frame 900 can include the facial landmarks 922, 924, and 926. The facial landmarks can include corners of a mouth, corners of eyes, eyebrow corners, the tip of the nose, nostrils, chin, the tips of ears, and so on. The performing of face detection on the second face can include performing facial landmark detection with the first frame from the video for the second face, and can include estimating a second rough bounding box for the second face based on the facial landmark detection. The estimating of a second rough bounding box can include the bounding box 920. Bounding boxes can also be estimated for one or more other faces within the boundary 910. The bounding box can be refined, as can one or more facial landmarks. The refining of the second set of locations for the second set of facial landmarks can be based on localized information around the second set of facial landmarks. The bounding box 920 and the facial landmarks 922, 924, and 926 can be used to estimate future locations for the second set of locations for the second set of facial landmarks in a future video frame from the first video frame. Techniques can include collecting second mental state data from a second individual involved in the game and analyzing the second mental state data to produce second mental state information from the second individual wherein the modifying the game based is further based on the second mental state information.

A second video frame 902 is also shown. The second video frame 902 includes a frame boundary 930, a first face 932, and a second face 934. The second video frame 902 also includes a bounding box 940 and the facial landmarks 942, 944, and 946. In other embodiments, multiple facial landmarks are generated and used for facial tracking of the two or more faces of a video frame, such as the shown second video frame 902. Facial points from the first face can be distinguished from other facial points. In embodiments, the other facial points include facial points of one or more other faces. The facial points can correspond to the facial points of the second face. The distinguishing of the facial points of the first face and the facial points of the second face can be used to distinguish between the first face and the second face, to track either or both of the first face and the second face, and so on. Other facial points can correspond to the second face. As mentioned above, multiple facial points can be determined within a frame. One or more of the other facial points that are determined can correspond to a third face. The location of the bounding box 940 can be estimated, where the estimating can be based on the location of the generated bounding box 920 shown in the first video frame 900. The three facial points shown, facial points 942, 944, and 946, might lie within the bounding box 940 or might not lie partially or completely within the bounding box 940. For instance, the second face 934 might have moved between the first video frame 900 and the second video frame 902. Based on the accuracy of the estimating of the bounding box 940, a new estimation can be determined for a third, future frame from the video, and so on. The evaluation can be performed, all or in part, on semiconductor based logic.

Figure 10:
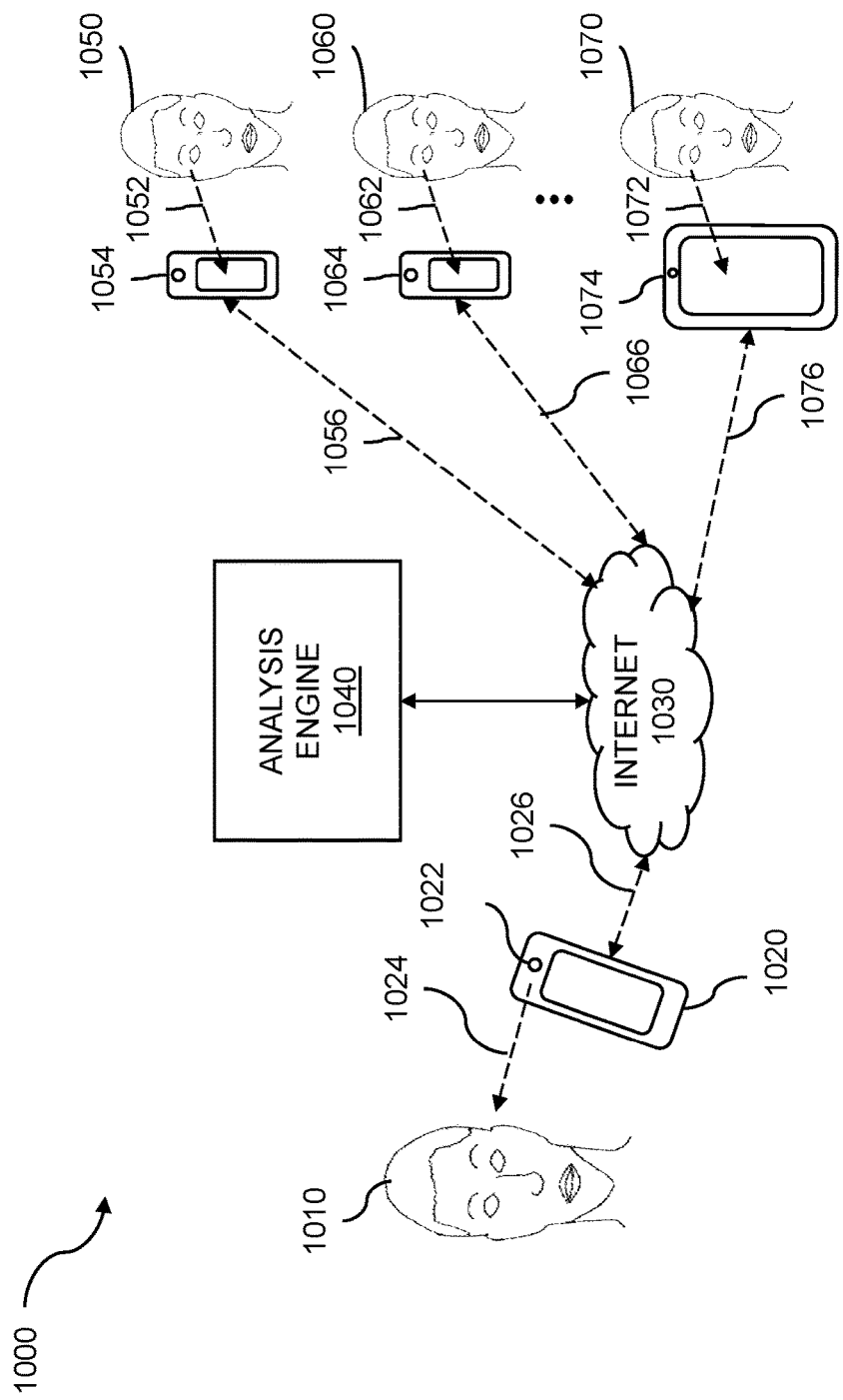
FIG. 10 shows live streaming of social video.

FIG. 10 shows live streaming of social video. The live streaming of social video can be performed for evaluating mental states. The evaluating of mental states can be based on using affect within a gaming context. The mental states of multiple people can be evaluated as they interact with a gaming environment. A video of a person or people can be transmitted via live streaming and information on emotions or moods. The live streaming of social video can be based on sub-sectional components. The sub-sectional components can be used to provide a context. The streaming and analysis can be facilitated by a video capture device, a local server, a remote server, a semiconductor based logic, and so on. The streaming can be live streaming and can include mental state analysis, mental state event signature analysis, etc. Live streaming video is an example of one-to-many social media, where video can be sent over the Internet from one person to a plurality of people using a social media app and/or platform. Live streaming is one of numerous popular techniques used by people who want to disseminate ideas, send information, provide entertainment, share experiences, and so on. Some of the live streams can be scheduled, such as webcasts, online classes, sporting events, news, computer gaming, or video conferences, while others can be impromptu streams that are broadcasted as needed or when desirable. Examples of impromptu live-stream videos can range from individuals simply wanting to share experiences with their social media followers, to live coverage of breaking news, emergencies, or natural disasters. The latter coverage is known as mobile journalism, or "mo jo", and is becoming increasingly common. With this type of coverage, "reporters" can use networked, portable electronic devices to provide mobile journalism content to a plurality of social media followers. Such reporters can be quickly and inexpensively deployed as the need or desire arises.

Several live-streaming social media apps and platforms can be used for transmitting video. One such video social media app is Meerkat™ that can link with a user's Twitter™ account. Meerkat™ enables a user to stream video using a handheld, networked electronic device coupled to video capabilities. Viewers of the live stream can comment on the stream using tweets that can be seen by and responded to by the broadcaster. Another popular app is Periscope™ that can transmit a live recording from one user to that user's Periscope™ account and other followers. The Periscope™ app can be executed on a mobile device. The user's Periscope™ followers can receive an alert whenever that user begins a video transmission. Another live-stream video platform is Twitch™ that can be used for video streaming of video gaming and broadcasts of various competitions and events.

The example 1000 shows a user 1010 broadcasting a video live stream to one or more people as shown by the person 1050, the person 1060, and the person 1070. A portable, network-enabled electronic device 1020 can be coupled to a forward-facing camera 1022. The portable electronic device 1020 can be a smartphone, a PDA, a tablet, a laptop computer, and so on. The camera 1022 coupled to the device 1020 can have a line-of-sight view 1024 to the user 1010 and can capture video of the user 1010. The captured video can be sent to an analysis or recommendation engine 1040 using a network link 1026 to the Internet 1030. The network link can be a wireless link, a wired link, and so on. The recommendation engine 1040 can recommend to the user 1010 an app and/or platform that can be supported by the server and can be used to provide a video live stream to one or more followers of the user 1010. In the example 1000, the user 1010 has three followers: the person 1050, the person 1060, and the person 1070. Each follower has a line-of-sight view to a video screen on a portable, networked electronic device. In other embodiments, one or more followers follow the user 1010 using any other networked electronic device, including a computer. In the example 1000, the person 1050 has a line-of-sight view 1052 to the video screen of a device 1054; the person 1060 has a line-of-sight view 1062 to the video screen of a device 1064, and the person 1070 has a line-of-sight view 1072 to the video screen of a device 1074. The portable electronic devices 1054, 1064, and 1074 can each be a smartphone, a PDA, a tablet, and so on. Each portable device can receive the video stream being broadcasted by the user 1010 through the Internet 1030 using the app and/or platform that can be recommended by the recommendation engine 1040. The device 1054 can receive a video stream using the network link 1056, the device 1064 can receive a video stream using the network link 1066, the device 1074 can receive a video stream using the network link 1076, and so on. The network link can be a wireless link, a wired link, a hybrid link, and so on. Depending on the app and/or platform that can be recommended by the recommendation engine 1040, one or more followers, such as the followers 1050, 1060, 1070, and so on, can reply to, comment on, and otherwise provide feedback to the user 1010 using their devices 1054, 1064, and 1074, respectively.

The human face provides a powerful communications medium through its ability to exhibit a myriad of expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined, including affect valence, spontaneous reactions, facial action units, and so on. The parameters that are determined can be used to infer or predict emotional and mental states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device or can each be using one or more devices for video capture. The videos that are collected can be collected using a web-based framework. The web-based framework can be used to display the video media presentation or event as well as to collect videos from multiple viewers who are online. That is, the collection of videos can be crowdsourced from those viewers who elected to opt-in to the video data collection.

The videos captured from the various viewers who chose to opt-in can be substantially different in terms of video quality, frame rate, etc. As a result, the facial video data can be scaled, rotated, and otherwise adjusted to improve consistency. Human factors further play into the capture of the facial video data. The facial data that is captured might or might not be relevant to the video media presentation being displayed. For example, the viewer might not be paying attention, might be fidgeting, might be distracted by an object or event near the viewer, or otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include items such as eyeglasses (because of reflections), eye patches, jewelry, and clothing that occludes or obscures the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. These AUs can be used to recognize emotions experienced by the observed person. Emotion-related facial actions can be identified using the emotional facial action coding system (EMFACS) and the facial action coding system affect interpretation dictionary (FACSAID). For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular mental and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated, as well as specific emotions, moods, or mental states.

The coding of faces identified in videos captured of people observing an event can be automated. The automated systems can detect facial AUs or discrete emotional states. The emotional states can include amusement, fear, anger, disgust, surprise, and sadness. The automated systems can be based on a probability estimate from one or more classifiers, where the probabilities can correlate with an intensity of an AU or an expression. The classifiers can be used to identify into which of a set of categories a given observation can be placed. In some cases, the classifiers can be used to determine a probability that a given AU or expression is present in a given frame of a video. The classifiers can be used as part of a supervised machine learning technique, where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from illumination or shadowing changes between and among video frames. The HoG can be computed on the image or on an adjusted version of the image, where the adjustment of the image can include scaling, rotation, etc. The image can be adjusted by flipping the image around a vertical line through the middle of a face in the image. The symmetry plane of the image can be determined from the tracker points and landmarks of the image.

In embodiments, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including a symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers perform the classification, including classifiers such as support vector machines (SVM) and random forests. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBP) and Local Gabor Binary Patterns (LGBP). The HoG descriptor represents the face as a distribution of intensity gradients and edge directions, and is robust in its ability to translate and scale. Differing patterns, including groupings of cells of various sizes and arranged in variously sized cell blocks, can be used. For example, 4×4 cell blocks of 8×8 pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis. This grouping and other analyses can be facilitated via semiconductor based logic.

Figure 11:
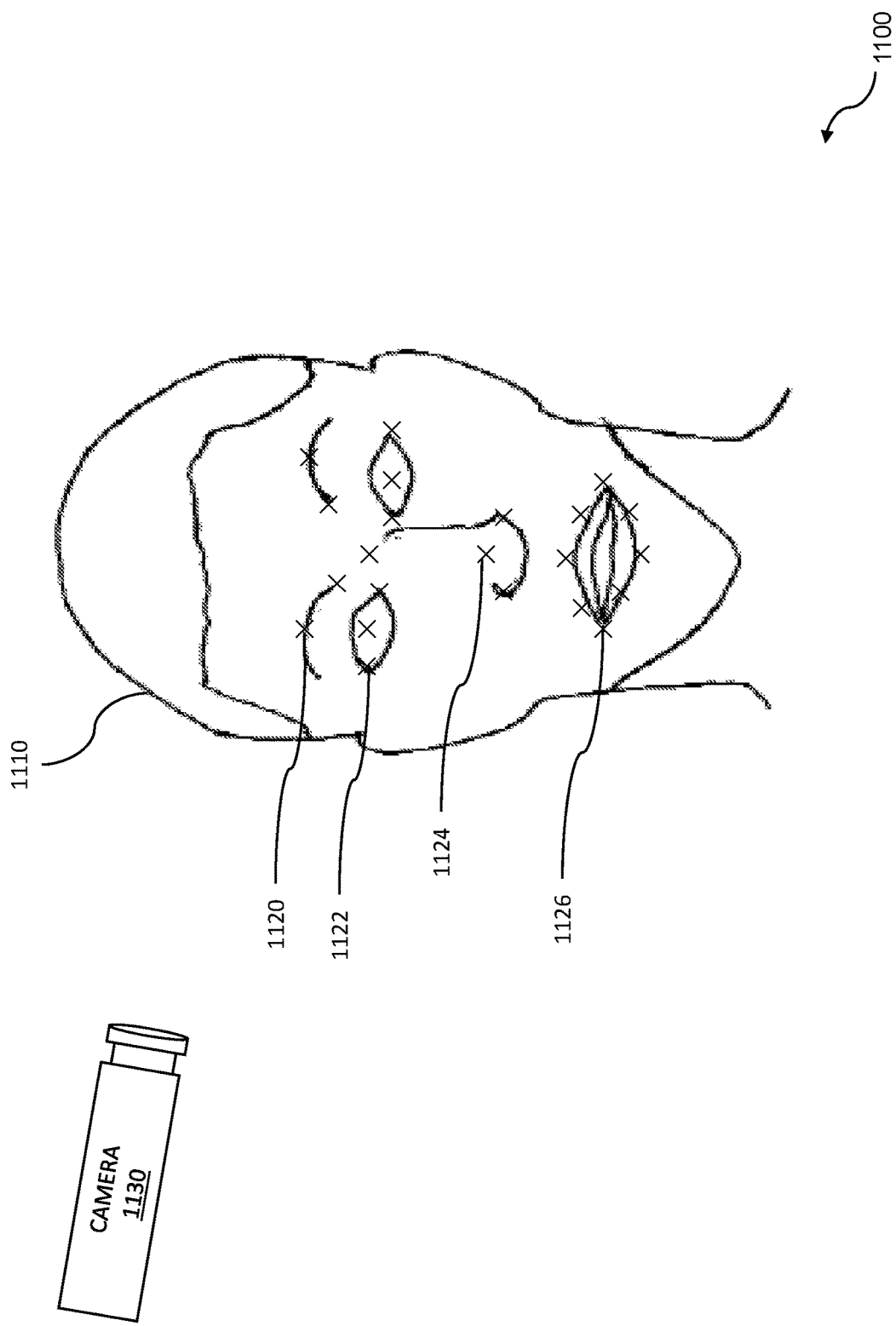
FIG. 11 shows example facial data collection including landmarks.

FIG. 11 shows example facial data collection including landmarks. The facial data including landmarks can be collected for evaluating mental states. The evaluating of mental states can be based on using affect within a gaming context. The mental states of multiple people can be evaluated as they interact with a gaming environment. In the example 1100, facial data including facial landmarks can be collected using a variety of electronic hardware and software techniques. The collecting of facial data including landmarks can be based on sub-sectional components of a population. The sub-sectional components can be used with performing the evaluation of content of the face, identifying facial landmarks, etc. The sub-sectional components can be used to provide a context. A face 1110 can be observed using a camera 1130 in order to collect facial data that includes facial landmarks. The facial data can be collected from a plurality of people using one or more of a variety of cameras. As previously discussed, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The quality and usefulness of the facial data that is captured can depend on the position of the camera 1130 relative to the face 1110, the number of cameras used, the illumination of the face, etc. In some cases, if the face 1110 is poorly lit or over-exposed (e.g. in an area of bright light), the processing of the facial data to identify facial landmarks might be rendered more difficult. In another example, the camera 1130 being positioned to the side of the person might prevent capture of the full face. Other artifacts can degrade the capture of facial data. For example, the person's hair, prosthetic devices (e.g. glasses, an eye patch, and eye coverings), jewelry, and clothing can partially or completely occlude or obscure the person's face. Data relating to various facial landmarks can include a variety of facial features. The facial features can comprise an eyebrow 1120, an outer eye edge 1122, a nose 1124, a corner of a mouth 1126, and so on. Multiple facial landmarks can be identified from the facial data that is captured. The facial landmarks that are identified can be analyzed to identify facial action units. The action units that can be identified can include AU02 outer brow raiser, AU14 dimpler, AU17 chin raiser, and so on. Multiple action units can be identified. The action units can be used alone and/or in combination to infer one or more mental states and emotions. A similar process can be applied to gesture analysis (e.g. hand gestures) with all of the analysis being accomplished or augmented by a mobile device, a server, semiconductor-based logic, and so on.

Figure 12:
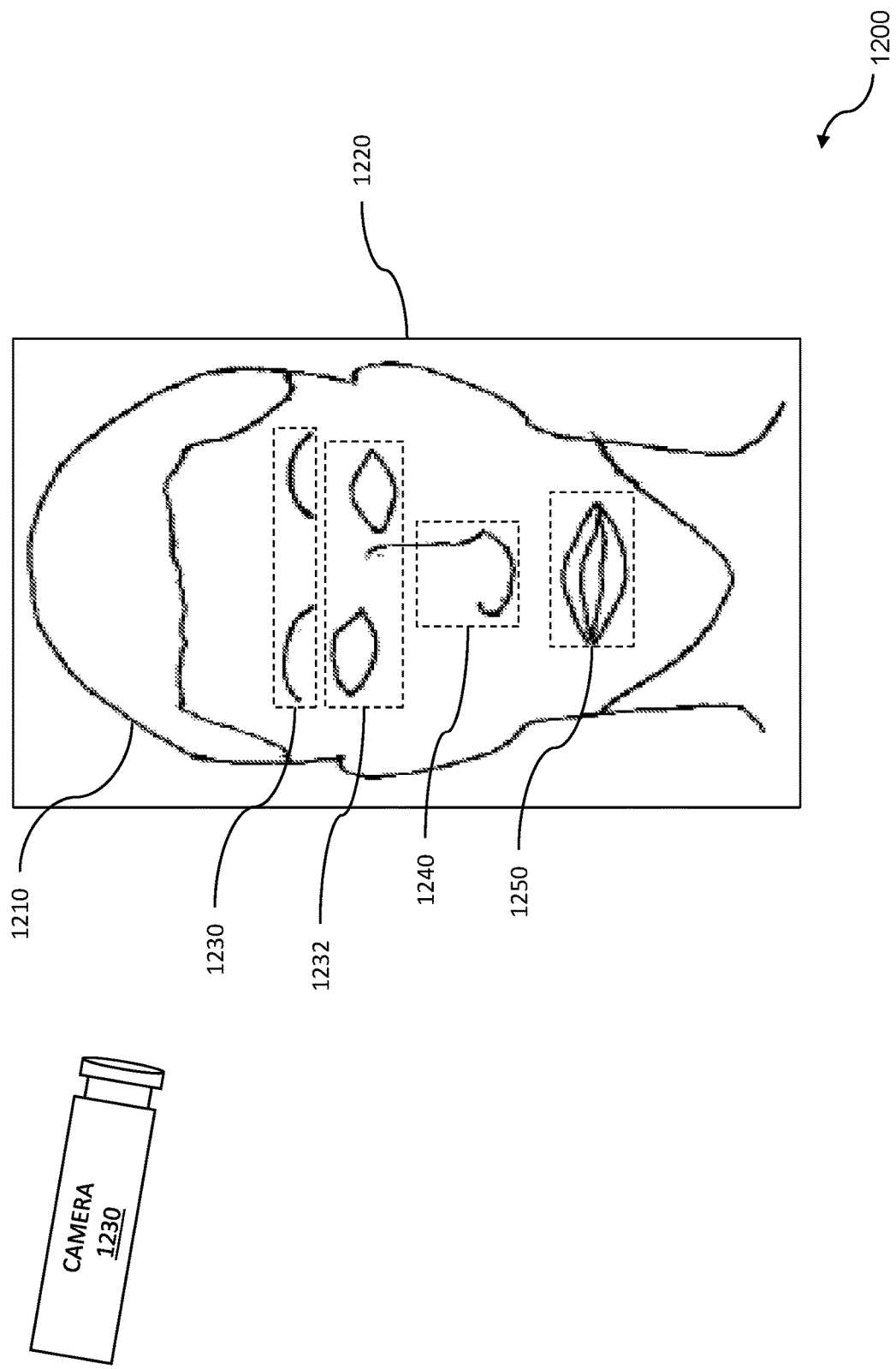
FIG. 12 shows example facial data collection including regions.

FIG. 12 shows example facial data collection including regions. The facial data including regions can be collected for evaluating mental states. The evaluating of mental states can be based on using affect within a gaming context. The mental states of multiple people can be evaluated as they interact with a gaming environment. Various regions of a face can be identified and used for a variety of purposes including facial recognition, facial analysis, and so on. The collecting of facial data including regions can be based on sub-sectional components of a population. The sub-sectional components can be used with performing the evaluation of content of the face, identifying facial regions, etc. The sub-sectional components can be used to provide a context. Facial analysis can be used to determine, predict, estimate, etc. mental states, emotions, and so on of a person from whom facial data can be collected. The one or more emotions that can be determined by the analysis can be represented by an image, a figure, an icon, etc. The representative icon can include an emoji. One or more emoji can be used to represent a mental state, a mood, etc. of an individual, to represent food, a geographic location, weather, and so on. The emoji can include a static image. The static image can be a predefined size such as a certain number of pixels. The emoji can include an animated image. The emoji can be based on a GIF or another animation standard. The emoji can include a cartoon representation. The cartoon representation can be any cartoon type, format, etc. that can be appropriate to representing an emoji. In the example 1200, facial data can be collected, where the facial data can include regions of a face. The facial data that is collected can be based on sub-sectional components of a population. When more than one face can be detected in an image, facial data can be collected for one face, some faces, all faces, and so on. The facial data which can include facial regions can be collected using any of a variety of electronic hardware and software techniques. The facial data can be collected using sensors including motion sensors, infrared sensors, physiological sensors, imaging sensors, and so on. A face 1210 can be observed using a camera 1230, a sensor, a combination of cameras and/or sensors, and so on. The camera 1230 can be used to collect facial data that can determine that a face is present in an image. When a face is present in an image, a bounding box 1220 can be placed around the face. Placement of the bounding box around the face can be based on detection of facial landmarks. The camera 1230 can be used to collect facial data from the bounding box 1220, where the facial data can include facial regions. The facial data can be collected from a plurality of people using any of a variety of cameras. As discussed previously, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. As discussed previously, the quality and usefulness of the facial data that is captured can depend on, among other examples, the position of the camera 1230 relative to the face 1210, the number of cameras and/or sensors used, the illumination of the face, any obstructions to viewing the face, and so on.

The facial regions that can be collected by the camera 1230, sensor, or combination of cameras and/or sensors can include any of a variety of facial features. The facial features that can be included in the facial regions that are collected can include eyebrows 1230, eyes 1232, a nose 1240, a mouth 1250, ears, hair, texture, and so on. Multiple facial features can be included in one or more facial regions. The number of facial features that can be included in the facial regions can depend on the desired amount of data to be captured, whether a face is in profile, whether the face is partially occluded or obstructed, etc. The facial regions that can include one or more facial features can be analyzed to determine facial expressions. The analysis of the facial regions can also include determining probabilities of occurrence of one or more facial expressions. The facial features that can be analyzed can also include textures, gradients, colors, shapes, etc. The facial features can be used to determine demographic data, where the demographic data can include age, ethnicity, culture, gender, etc. Multiple textures, gradients, colors, shapes, and so on, can be detected by the camera 1230, sensor, or combination of cameras and sensors. Texture, brightness, and color, for example, can be used to detect boundaries in an image for detection of a face, facial features, facial landmarks, and so on.

A texture in a facial region can include facial characteristics, skin types, and so on. In some instances, a texture in a facial region can include smile lines, crow's feet, wrinkles, and so on. Another texture that can be used to evaluate a facial region can include a smooth portion of skin such as a smooth portion of a check. A gradient in a facial region can include values assigned to local skin texture, shading, etc. A gradient can be used to encode a texture by computing magnitudes in a local neighborhood or portion of an image. The computed values can be compared to discrimination levels, threshold values, and so on. The gradient can be used to determine gender, facial expression, etc. A color in a facial region can include eye color, skin color, hair color, and so on. A color can be used to determine demographic data, where the demographic data can include ethnicity, culture, age, gender, etc. A shape in a facial region can include the shape of a face, eyes, nose, mouth, ears, and so on. As with color in a facial region, shape in a facial region can be used to determine demographic data including ethnicity, culture, age, gender, and so on.

The facial regions can be detected based on detection of edges, boundaries, and so on, of features that can be included in an image. The detection can be based on various types of analysis of the image. The features that can be included in the image can include one or more faces. A boundary can refer to a contour in an image plane, where the contour can represent ownership of a particular picture element (pixel) from one object, feature, etc. in the image, to another object, feature, and so on, in the image. An edge can be a distinct, low-level change of one or more features in an image. That is, an edge can be detected based on a change, including an abrupt change, in color, brightness, etc. within an image. In embodiments, image classifiers are used for the analysis. The image classifiers can include algorithms, heuristics, and so on, and can be implemented using functions, classes, subroutines, code segments, etc. The classifiers can be used to detect facial regions, facial features, and so on. As discussed above, the classifiers can be used to detect textures, gradients, color, shapes, edges, etc. Any classifier can be used for the analysis including but not limited to density estimation, support vector machines (SVM), logistic regression, classification trees, and so on. By way of example, consider facial features that can include the eyebrows 1230. One or more classifiers can be used to analyze the facial regions that can include the eyebrows to determine a probability for either a presence or an absence of an eyebrow furrow. The probability can include a posterior probability, a conditional probability, and so on. The probabilities can be based on Bayesian Statistics or another statistical analysis technique. The presence of an eyebrow furrow can indicate the person from whom the facial data can be collected is annoyed, confused, unhappy, and so on. In another example, consider facial features that include a mouth 1250. One or more classifiers can be used to analyze the facial region that can include the mouth to determine a probability for either a presence or an absence of mouth edges turned up to form a smile. Multiple classifiers can be used to determine one or more facial expressions. Techniques can include identifying a face of the individual; determining regions within the face of the individual; and evaluating the regions for emotional content.

Figure 13:
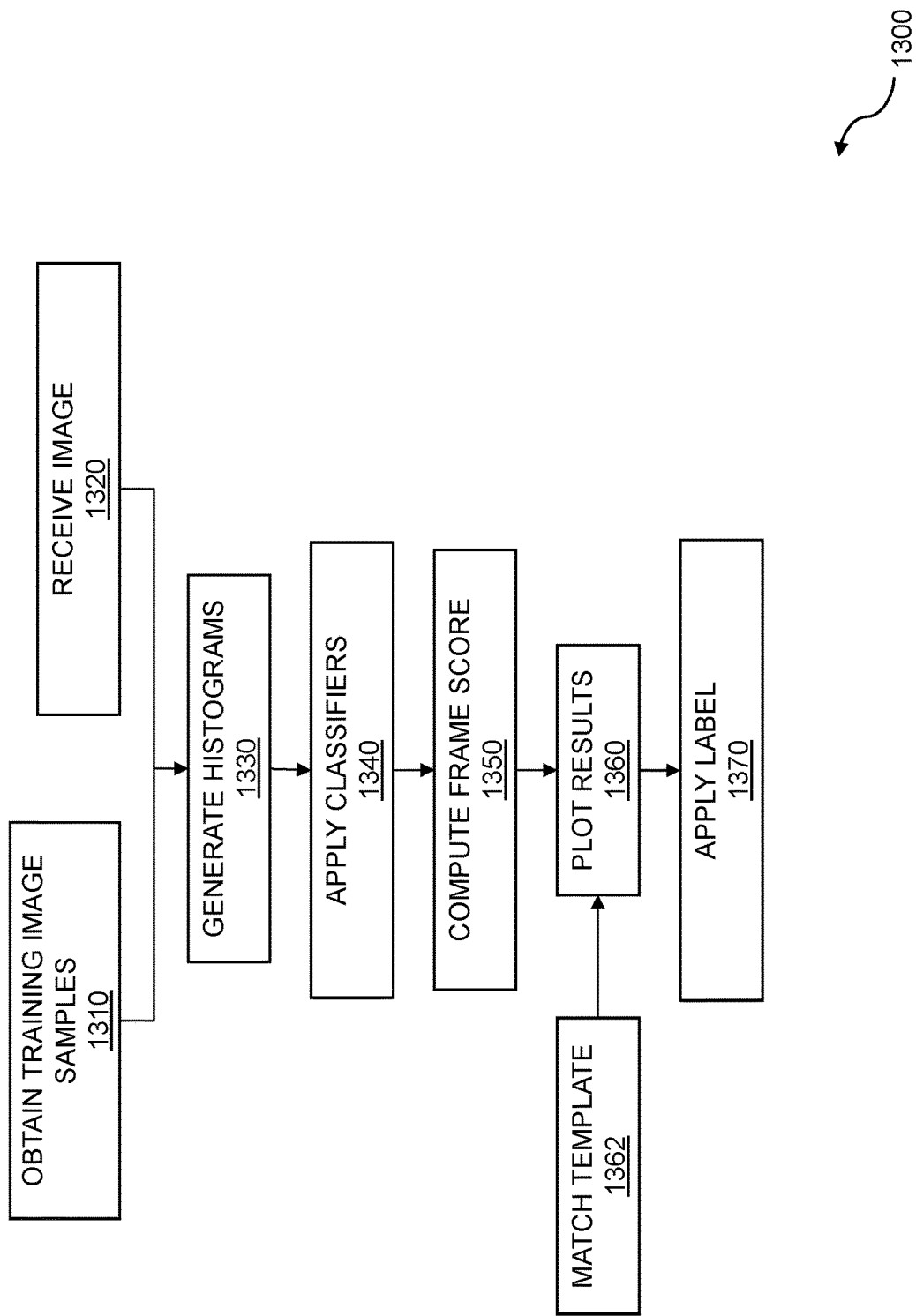
FIG. 13 is a flow diagram for detecting facial expressions.

FIG. 13 is a flow diagram for detecting facial expressions that can be used for analysis within a gaming context. The facial expressions can be detected for evaluating mental states. The evaluating of mental states can be used within a gaming context in order to modify tasks presented to a player. The mental states of multiple people can be evaluated as they interact with a gaming environment. The sub-sectional components can be used with performing the detecting facial expressions. The sub-sectional components can be used to provide a context. The flow 1300, or portions thereof, can be implemented in semiconductor logic, can be accomplished using a mobile device, can be accomplished using a server device, and so on. The flow 1300 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on determination of action units (AU), where the action units are determined using FACS coding. The AUs can be used singly or in combination to identify facial expressions. Based on the facial landmarks, one or more AUs can be identified by number and intensity. For example, AU12 can be used to code a lip corner puller and can be used to infer a smirk.

The flow 1300 begins by obtaining training image samples 1310. The image samples can include a plurality of images of one or more people. Human coders who are trained to correctly identify AU codes based on the FACS can code the images. The training or "known good" images can be used as a basis for training a machine learning technique. Once trained, the machine learning technique can be used to identify AUs in other images that can be collected using a camera, a sensor, and so on. The flow 1300 continues with receiving an image 1320. The image 1320 can be received from a camera, a sensor, and so on. As previously discussed, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The image that is received can be manipulated in order to improve the processing of the image. For example, the image can be cropped, scaled, stretched, rotated, flipped, etc. in order to obtain a resulting image that can be analyzed more efficiently. Multiple versions of the same image can be analyzed. In some cases, the manipulated image and a flipped or mirrored version of the manipulated image can be analyzed alone and/or in combination to improve analysis. The flow 1300 continues with generating histograms 1330 for the training images and the one or more versions of the received image. The histograms can be based on a HoG or another histogram. As described in previous paragraphs, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video.

The flow 1300 continues with applying classifiers 1340 to the histograms. The classifiers can be used to estimate probabilities, where the probabilities can correlate with an intensity of an AU or an expression. In some embodiments, the choice of classifiers used is based on the training of a supervised learning technique to identify facial expressions. The classifiers can be used to identify into which of a set of categories a given observation can be placed. The classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of multiple AUs can be determined. The flow 1300 continues with computing a frame score 1350. The score computed for an image, where the image can be a frame from a video, can be used to determine the presence of a facial expression in the image or video frame. The score can be based on one or more versions of the image 1320 or a manipulated image. The score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The classifier that is used can be used to identify symmetrical facial expressions (e.g. smile), asymmetrical facial expressions (e.g. outer brow raiser), and so on.

The flow 1300 continues with plotting results 1360. The results that are plotted can include one or more scores for one or more frames computed over a given time t. For example, the plotted results can include classifier probability results from analysis of HoGs for a sequence of images and video frames. The plotted results can be matched with a template 1362. The template can be temporal and can be represented by a centered box function or another function. A best fit with one or more templates can be found by computing a minimum error. Other best-fit techniques can include polynomial curve fitting, geometric curve fitting, and so on. The flow 1300 continues with applying a label 1370. The label can be used to indicate that a particular facial expression has been detected in the one or more images or video frames which constitute the image that was received 1320. The label can be used to indicate that any of a range of facial expressions has been detected, including a smile, an asymmetric smile, a frown, and so on. Various steps in the flow 1300 may be changed in order, repeated, omitted, or the like without departing from the disclosed concepts. Various embodiments of the flow 1300 can be included in a computer program product embodied in a non-transitory computer readable medium that includes code executable by one or more processors. Various embodiments of the flow 1300, or portions thereof, can be included on a semiconductor chip and implemented in special purpose logic, programmable logic, and so on.

Various rendering or graphical displays are possible to aid in the analysis of mental state. The renderings can compare metrics for various mental states with norms for those mental states. Numerous thumbnails can be shown along with metrics and norms for media presentations represented by the thumbnails. In some embodiments, the thumbnails are replaced by short video clips or other representations of the media presentations analyzed. Other types of selections besides countries can be included such as region, socioeconomic group, race, ethnicity, language group, market, age, gender, emotional tone, media type, media duration, demographic, device, product category and so on. In some cases multiple selections can be made, or selections and sub-selections can be chosen.

When a metric value is significantly different from a norm value a demarcation can be included such as a colored dot. With a much higher valence indicating a much more positive than normal response, an advertisement can be expected perform at a higher level and therefore be much more effective. A significantly worse metric can be indicated by a dot of another color, such as red. For example, for an advertisement with a higher-than-typical mean and a lower-than-typical variance, the vast majority of responses will be clustered at the higher mean. Other observations can be denoted by other techniques such as bolding, dots of other colors, and the like. Analysis can be very narrow if desired. For example, a metric and norms can be provided for women, in Japan, responding to automotive advertisements, shown on a mobile device, that have a humorous emotional tone.

Various graphs can aid in understanding mental states and normal mental state responses for different regions or demographics. A smile can be used to understand enjoyment of an advertisement, for instance. But, in order to accurately interpret the data, it is important to have a norm value for the people observing the advertisement. The norm value can help identify typical results for a certain people, culture, gender, etc. Different norms can exist in different cultures and understanding these norms can aid in analysis. A norm can include a propensity to smile, a propensity to concentrate, a propensity to express, and so on.

A concentration graph can be useful in understanding how focused people are on a certain media presentation. Lack of concentration can indicate that an advertisement is not engaging people, for instance. A normative value can be critical in understanding people's responses. Understanding the different concentration expressiveness norms can aid in developing advertisements for different countries. Likewise, understanding norms for any other type of demographics can aid in market research analysis.

Figure 14:
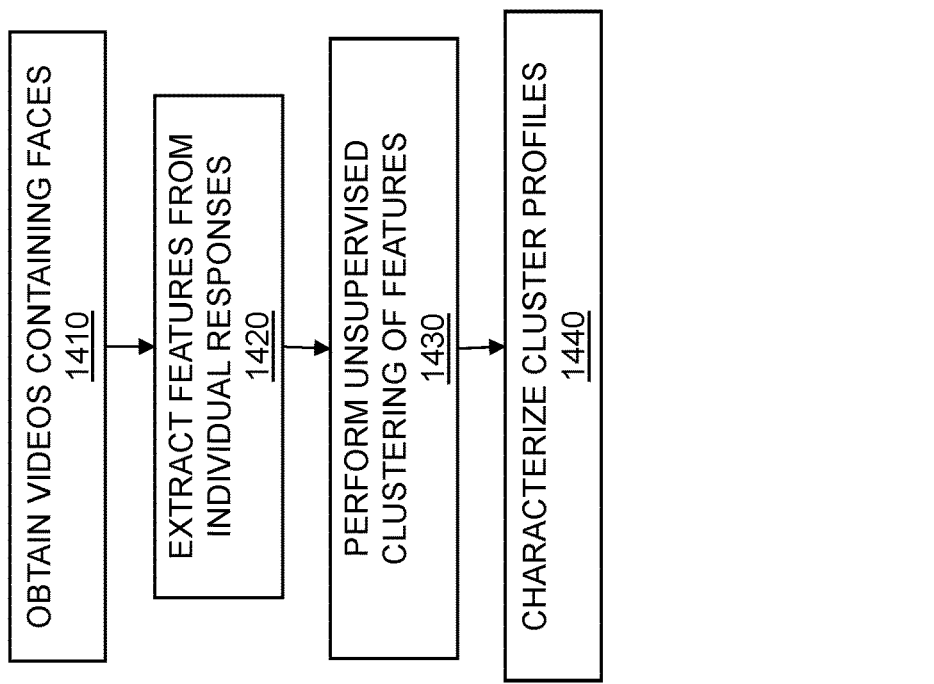
FIG. 14 is a flow diagram for the large-scale clustering of facial events.

FIG. 14 is a flow diagram for the large-scale clustering of facial events that can be used in conjunction with gaming based on emotions. The clustering and evaluation of facial events can be augmented using a mobile device, a server, semiconductor based logic, and so on. As discussed above, collection of facial video data from one or more people can include a web-based framework. The web-based framework can be used to collect facial video data from large numbers of people located over a wide geographic area. The web-based framework can include an opt-in feature that allows people to agree to facial data collection. The web-based framework can be used to render and display data to one or more people and can collect data from the one or more people. For example, the facial data collection can be based on showing one or more viewers a video media presentation through a website. The web-based framework can be used to display the video media presentation or event and to collect videos from multiple viewers who are online. That is, the collection of videos can be crowdsourced from those viewers who elected to opt-in to the video data collection. The video event can be a commercial, a political ad, an educational segment, and so on.

The flow 1400 begins with obtaining videos containing faces 1410. The videos can be obtained using one or more cameras, where the cameras can include a webcam coupled to one or more devices employed by the one or more people using the web-based framework. The flow 1400 continues with extracting features from the individual responses 1420. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 1400 continues with performing unsupervised clustering of features 1430. The unsupervised clustering can be based on an event. The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 1400 continues with characterizing cluster profiles 1440. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted-in can be collected. The characterization of the collected and analyzed video can depend in part on the number of smiles that occurred at various points throughout the humorous video. Similarly, the characterization can be performed on collected and analyzed videos of people viewing a news presentation. The characterized cluster profiles can be further analyzed based on demographic data. The number of smiles resulting from people viewing a humorous video can be compared to various demographic groups, where the groups can be formed based on geographic location, age, ethnicity, gender, and so on. Various steps in the flow 1400 may be changed in order, repeated, omitted, or the like without departing from the disclosed concepts. Various embodiments of the flow 1400 can be included in a computer program product embodied in a non-transitory computer readable medium that includes code executable by one or more processors. Various embodiments of the flow 1400, or portions thereof, can be included on a semiconductor chip and implemented in special purpose logic, programmable logic, and so on.

Figure 15:
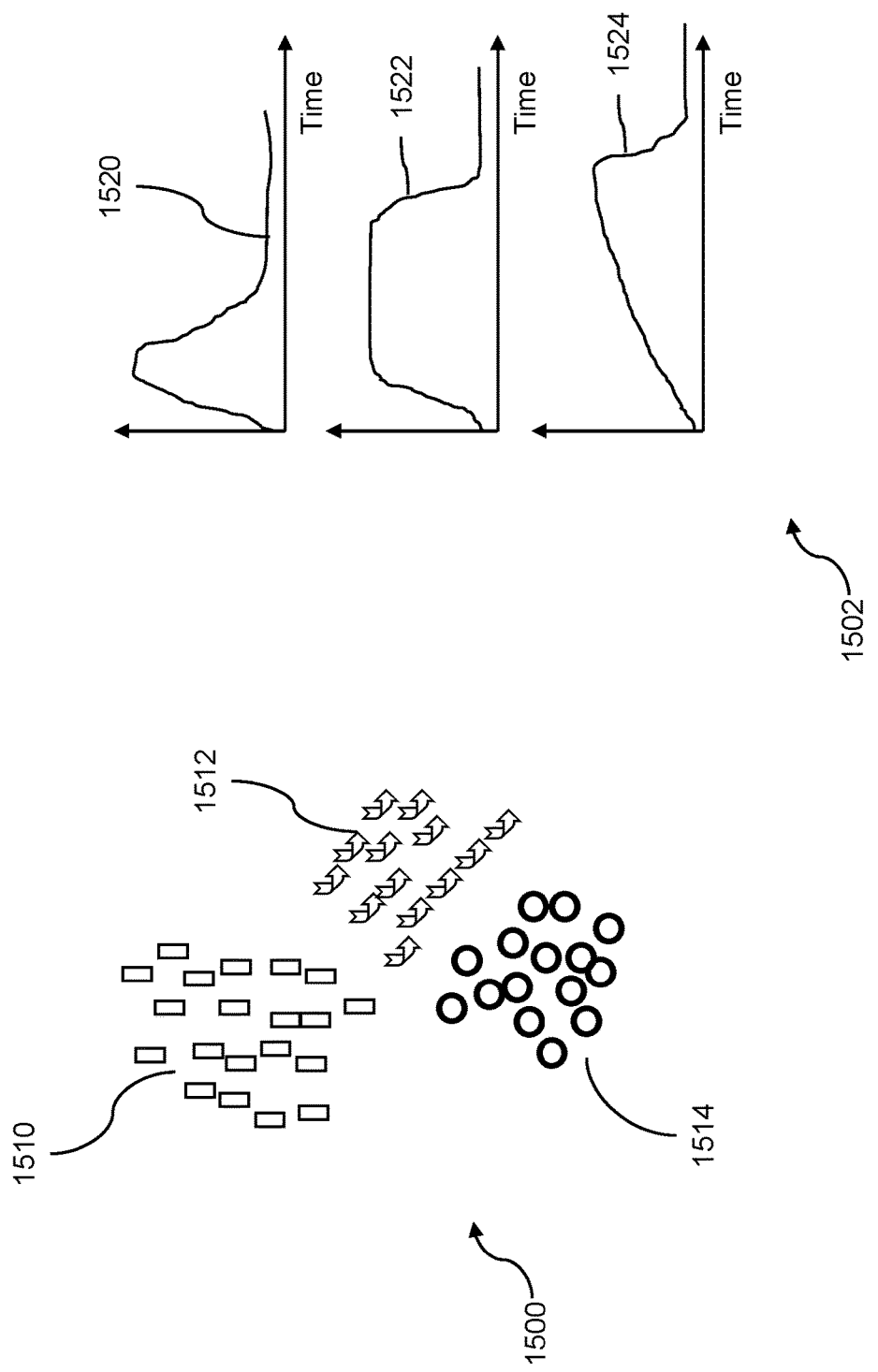
FIG. 15 shows unsupervised clustering of features and characterizations of cluster profiles.

FIG. 15 shows unsupervised clustering of features and characterizations of cluster profiles that can be used for gaming. The unsupervised clustering of features and characterizations of cluster profiles can be used for evaluating mental states. The mental states of multiple people can be evaluated as they interact with a gaming environment. Features including samples of facial data can be clustered using unsupervised clustering. Various clusters can be formed which include similar groupings of facial data observations. The example 1500 shows three clusters, clusters 1510, 1512, and 1514. The clusters can be based on video collected from people who have opted-in to video collection. When the data collected is captured using a web-based framework, the data collection can be performed on a grand scale, including hundreds, thousands, or even more participants who can be located locally and/or across a wide geographic area. Unsupervised clustering is a technique that can be used to process the large amounts of captured facial data and to identify groupings of similar observations. The unsupervised clustering can also be used to characterize the groups of similar observations. The characterizations can include identifying behaviors of the participants. The characterizations can be based on identifying facial expressions and facial action units of the participants. Some behaviors and facial expressions can include faster or slower onsets, faster or slower offsets, longer or shorter durations, etc. The onsets, offsets, and durations can all correlate to time. The data clustering that results from the unsupervised clustering can support data labeling. The labeling can include FACS coding. The clusters can be partially or totally based on a facial expression resulting from participants viewing a video presentation, where the video presentation can be an advertisement, a political message, educational material, a public service announcement, and so on. The clusters can be correlated with demographic information, where the demographic information can include educational level, geographic location, age, gender, income level, and so on.

The cluster profiles 1502 can be generated based on the clusters that can be formed from unsupervised clustering, with time shown on the x-axis and intensity or frequency shown on the y-axis. The cluster profiles can be based on captured facial data including facial expressions. The cluster profile 1520 can be based on the cluster 1510, the cluster profile 1522 can be based on the cluster 1512, and the cluster profile 1524 can be based on the cluster 1514. The cluster profiles 1520, 1522, and 1524 can be based on smiles, smirks, frowns, or any other facial expression. The emotional states of the people who have opted-in to video collection can be inferred by analyzing the clustered facial expression data. The cluster profiles can be plotted with respect to time and can show a rate of onset, a duration, and an offset (rate of decay). Other time-related factors can be included in the cluster profiles. The cluster profiles can be correlated with demographic information, as described above.

Figure 16A:
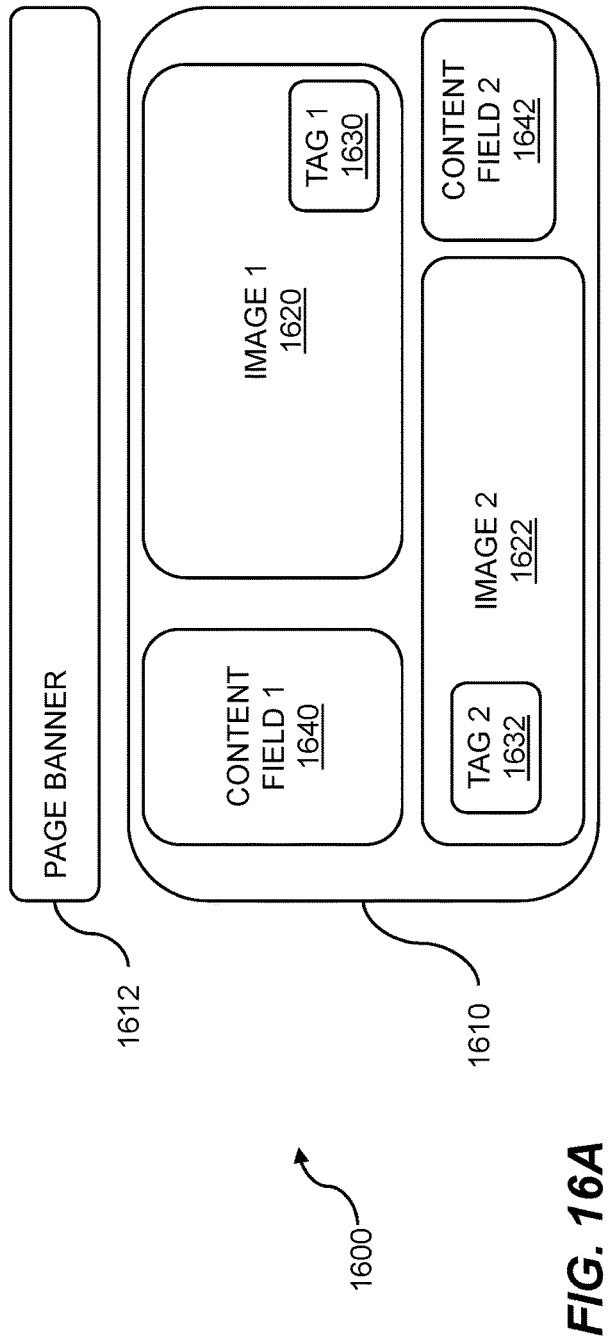
FIG. 16A shows example tags embedded in a webpage.

FIG. 16A shows example tags embedded in a webpage. The tags embedded in a webpage can be used for evaluating mental states. The evaluating of mental states can be used within a gaming context. The mental states of multiple people can be evaluated as they interact with one or more games. The webpage can contain analysis from sub-sectional components. The sub-sectional components can be used to provide a context. Once a tag is detected within a game or another page, a mobile device, a server, semiconductor based logic, etc. can be used to evaluate associated facial expressions. A webpage 1600 can include a page body 1610, a page banner 1612, and so on. The page body can include one or more objects, where the objects can include text, images, videos, audio, and so on. The example page body 1610 shown includes a first image, image 1 1620; a second image, image 2 1622; a first content field, content field 1 1640; and a second content field, content field 2 1642. In practice, the page body 1610 can contain multiple images and content fields, and can include one or more videos, one or more audio presentations, and so on. The page body can include embedded tags, such as tag 1 1630 and tag 2 1632. In the example shown, tag 1 1630 is embedded in image 1 1620, and tag 2 1632 is embedded in image 2 1622. In embodiments, multiple tags are imbedded. Tags can also be imbedded in content fields, in videos, in audio presentations, etc. When a user mouses over a tag or clicks on an object associated with a tag, the tag can be invoked. For example, when the user mouses over tag 1 1630, tag 1 1630 can then be invoked. Invoking tag 1 1630 can include enabling a camera coupled to a user's device and capturing one or more images of the user as the user views a media presentation (or digital experience). In a similar manner, when the user mouses over tag 2 1632, tag 2 1632 can be invoked. Invoking tag 2 1632 can also include enabling the camera and capturing images of the user. In other embodiments, other actions are taken based on invocation of the one or more tags. Invoking an embedded tag can initiate an analysis technique, post to social media, award the user a coupon or another prize, initiate mental state analysis, perform emotion analysis, and so on.

Figure 16B:
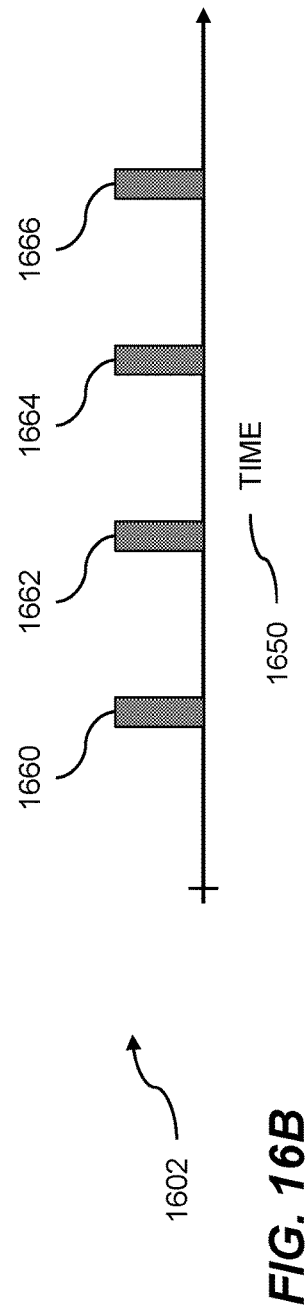
FIG. 16B shows invoking tags to collect images.

FIG. 16B shows invoking tags to collect images. The invoking tags to collect images can be used for evaluating mental states. The evaluating of mental states can be used in gaming. The mental states of multiple people can be evaluated as they interact with a gaming environment. The tags can be related to analysis using sub-sectional components. The sub-sectional components can be used to provide a context. As previously stated, a media presentation can be a video, a webpage, and so on. A video 1602 can include one or more embedded tags, such as a tag 1660, another tag 1662, a third tag 1664, a fourth tag 1666, and so on. In practice, multiple tags can be included in the media presentation. The one or more tags can be invoked during the media presentation. The collection of the invoked tags can occur over time, as represented by a timeline 1650. When a tag is encountered in the media presentation, the tag can be invoked. When the tag 1660, for example, is encountered, invoking the tag can enable a camera coupled to a user's device and can capture one or more images of the user viewing the media presentation. Invoking a tag can depend on opt-in by the user. For example, if a user has agreed to participate in a study by indicating an opt-in, then the camera coupled to the user's device can be enabled and one or more images of the user can be captured. If the user has not agreed to participate in the study and has not indicated an opt-in, then invoking the tag 1660 does not enable the camera nor capture images of the user during the media presentation. The user can indicate an opt-in for certain types of participation, where opting-in can be dependent on specific content in the media presentation. The user could opt-in to participation in a study of political campaign messages and not opt-in for a particular advertisement study. In this case, tags that are related to political campaign messages, advertising messages, social media sharing, etc. and that enable the camera and image capture when invoked would be embedded in the media presentation social media sharing, and so on. However, tags imbedded in the media presentation that are related to advertisements would not enable the camera when invoked. Various other situations of tag invocation are possible.

Figure 17:
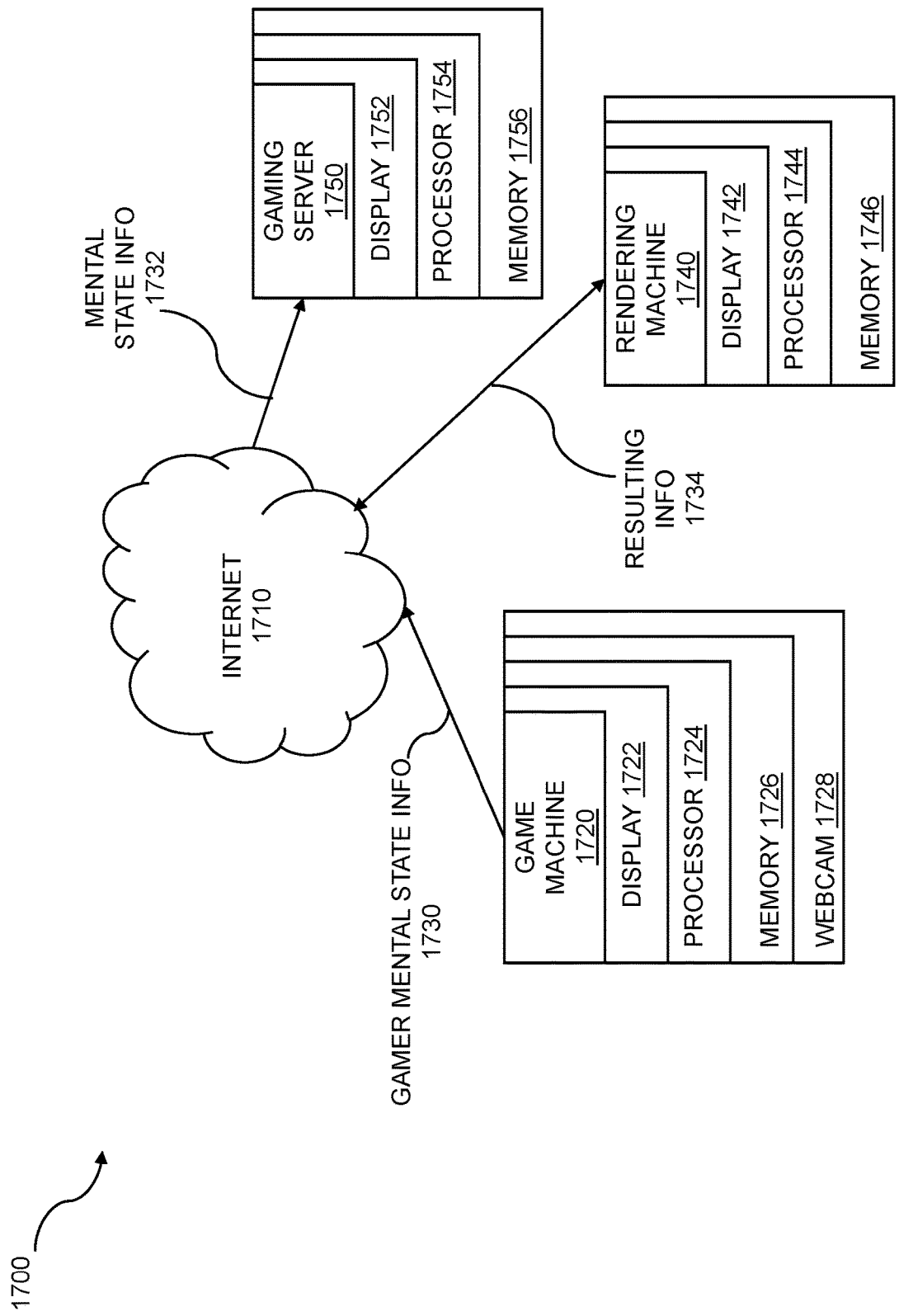
FIG. 17 is a system diagram for evaluating mental states.

FIG. 17 is a system diagram for evaluating mental states. The evaluating of mental states can use affect within a gaming context. The mental states of multiple people can be evaluated as they interact within a gaming environment. The system 1700 for evaluating mental states using affect within a gaming environment can be implemented using a variety of electronic hardware and software techniques. For example, the system 1700 for evaluating using affect within a gaming context can be implemented using one or more machines. An example of such a machine-based system is shown for gaming, game serving, and rendering. The Internet 1710, intranet, or another computer network can be used for communication between or among the various computers and/or machines involved in gaming. A game machine or client computer 1720 has a memory 1726 which stores instructions, and one or more processors 1724 attached to the memory 1726, wherein the one or more processors 1724 can execute instructions stored in the memory 1726. The memory 1726 can be used for storing instructions, for storing mental state data, for system support, gaming information, and the like. The game machine 1720 also can have an Internet connection to carry gamer mental state information 1730, and a display 1722 that can present one or more games. The game machine 1720 can collect mental state data from one or more people as they play a game or games. In some embodiments, there are multiple client computers that each collect mental state data from people as they participate in the game. The game machine 1720 can have a camera 1728, such as a webcam, for capturing an individual's interaction with a game, including video of the gamer. The camera 1728 can refer to a webcam, a camera on a computer (such as a laptop, a net-book, a tablet, or the like), a video camera, a still camera, a cell phone camera, a mobile device camera (including, but not limited to, a forward facing camera), a thermal imager, a CCD device, a three-dimensional camera, a depth camera, a light field camera, and multiple webcams used to capture different views of people who are gaming or any other type of image capture apparatus that can allow image data captured to be used by the electronic system.

As the mental state data is collected, the game machine 1720 can upload information to a gaming server 1750 or analysis computer, based on the mental state data from the plurality of people who play the game. The game machine 1720 can communicate with the gaming server 1750 over the Internet 1710, intranet, some other computer network, or by any other method suitable for communication between two computers. In some embodiments, parts of the gaming server 1750 functionality are embodied in the client computer. The gaming server 1750 can have a connection to the Internet 1710 to enable gaming and mental state information 1732 to be received by the gaming server 1750. The mental state information 1732 includes the gamer mental state information 1730 as well as mental state information from other gamers, in some embodiments. Further, the gaming server 1750 can have a memory 1756 which stores instructions, data, help information and the like, and one or more processors 1754 attached to the memory 1756 wherein the one or more processors 1754 can execute instructions. The gaming server 1750 can have a memory 1756 which stores instructions and one or more processors 1754 attached to the memory 1756 wherein the one or more processors 1754 can execute instructions. The memory 1756 can be used for storing instructions, for storing mental state data, for system support, and the like. The analysis computer can use its Internet, or another computer communication method, to obtain mental state information 1732. The gaming server 1750 can receive mental state information collected from a plurality of gamers from the game machines 1720, and can aggregate mental state information on the plurality of people who play the game.

The gaming server 1750 can process mental state data or aggregated mental state data gathered from a person or a plurality of people to produce mental state information about the person or a plurality of people. In some embodiments, the gaming server 1750 obtains gamer mental state information 1730 from the game machine 1720. In this case, the mental state data captured by the game machine 1720 was analyzed by the game machine 1720 to produce mental state information for uploading. In some embodiments, the gaming server 1750 receives or analyzes to generate aggregated mental state information based on the mental state data from the plurality of people who play the game and can present aggregated mental state information in a rendering on a display 1752. In some embodiments, the analysis computer is set up for receiving mental state data collected from a plurality of people as they play the game, in a real-time or near real-time embodiment. In at least one embodiment, a single computer incorporates the client, server and analysis functionality. Gamer mental state data can be collected from the game machine 1720 to form mental state information on the person or plurality of people playing the game. The system 1700 can include a computer program product embodied in a non-transitory computer readable medium for game play.

The rendering machine 1740 can render a variety of data including gamer mental state data 1730, mental state information 1732, game data, resulting information 1734, and so on. The rendering machine 1740 can include one or more processors 1744 coupled to a memory 1746 which can store and retrieve instructions, data, help information, etc., and can also include a display 1742. The rendering of the resulting gaming information rendering data 1734 can occur on the rendering machine 1740 or on a platform different from the rendering machine 1740. In embodiments, the rendering of the resulting gaming information rendering data occurs on the game machine 1720, on the gaming server 1750, or on both the game machine 1720 and the gaming server 1750. As shown in the system 1700, the rendering machine 1740 can receive resulting gaming information rendering data 1734 via the Internet 1710, intranet, or another network from the game machine 1720, from the gaming server 1750, or from both. The rendering can include a visual display or any other appropriate display format. The system 1700 can include computer program product stored on a non-transitory computer-readable medium for gaming, the computer program product comprising: code for collecting mental state data, wherein the mental state data includes facial data, captured by a webcam, of an individual while the individual is involved in a game; code for analyzing the mental state data to produce mental state information; and code for modifying the game based on the mental state information, wherein the modifying the game includes changing tasks with which the individual is presented, based on a threshold.

Each of the above methods may be executed on one or more processors on one or more computer systems. Embodiments may include various forms of distributed computing, client/server computing, and cloud based computing. Further, it will be understood that for each flowchart in this disclosure, the depicted steps or boxes are provided for purposes of illustration and explanation only. The steps may be modified, omitted, or re-ordered and other steps may be added without departing from the scope of this disclosure. Further, each step may contain one or more sub-steps. While the foregoing drawings and description set forth functional aspects of the disclosed systems, no particular arrangement of software and/or hardware for implementing these functional aspects should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. Each element of the block diagrams and flowchart illustrations, as well as each respective combination of elements in the block diagrams and flowchart illustrations, illustrates a function, step or group of steps of the methods, apparatus, systems, computer program products and/or computer-implemented methods. Any and all such functions may be implemented by computer program instructions, by special-purpose hardware-based computer systems, by combinations of special purpose hardware and computer instructions, by combinations of general purpose hardware and computer instructions, by a computer system, and so on. Any and all of which implementations may be generally referred to herein as a "circuit," "module," or "system."

A programmable apparatus that executes any of the above mentioned computer program products or computer implemented methods may include one or more processors, microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are not limited to applications involving conventional computer programs or programmable apparatus that run them. It is contemplated, for example, that embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized. The computer readable medium may be a non-transitory computer readable medium for storage. A computer readable storage medium may be electronic, magnetic, optical, electromagnetic, infrared, semiconductor, or any suitable combination of the foregoing. Further computer readable storage medium examples may include an electrical connection having one or more wires, a portable computer diskette, a hard disk, a random access memory (RAM), a read-only memory (ROM), an erasable programmable read-only memory (EPROM), Flash, MRAM, FeRAM, phase change memory, an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. Each thread may spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the entity causing the step to be performed.

While the invention has been disclosed in connection with preferred embodiments shown and described in detail, various modifications and improvements thereon will become apparent to those skilled in the art. Accordingly, the spirit and scope of the present invention is not to be limited by the foregoing examples, but is to be understood in the broadest sense allowable by law.

What is claimed is:

1. A computer implemented method for gaming comprising:
collecting mental state data, wherein the mental state data includes facial data, captured by a webcam, of an individual while the individual is involved in a game;
analyzing the mental state data to produce mental state information; and
modifying the game based on the mental state information, wherein the modifying the game includes changing tasks with which the individual is presented, based on a threshold, wherein the threshold represents a norm for a demographic of the individual, and wherein the modifying the game further includes modifying an avatar that represents the individual.

2. The method of claim 1 wherein the mental state data further comprises physiological data collected via the webcam.

3. The method of claim 1 wherein the collecting mental state data further comprises collecting actigraphy data.

4. The method of claim 1 wherein the threshold comprises a divider in the mental state information that provides for dividing respondents into those respondents that had higher reactions from those with lower reactions.

5. The method of claim 1 wherein the analyzing of the mental state data is accomplished, at least in part, using a web services server.

6. The method of claim 1 wherein the modifying the avatar includes modifying a face on the avatar.

7. The method of claim 6 wherein the modifying the avatar includes modifying a facial expression of the avatar.

8. The method of claim 7 wherein the modifying the facial expression of the avatar includes having the face of the avatar mimic a face of the individual involved in a game.

9. The method of claim 6 wherein the modifying the face of the avatar includes having portions of the face of the avatar track landmarks of a face of the individual involved in a game.

10. The method of claim 1 wherein the modifying the avatar includes having the avatar mimic a mood of the individual involved in a game.

11. The method of claim 1 wherein the avatar is animated based on the mental state information.

12. The method of claim 1 wherein the game is a multiplayer game.

13. The method of claim 12 wherein the modifying the game includes modifying an avatar that represents a group of people who are playing the multiplayer game.

14. The method of claim 13 wherein the avatar represents a collective mental state for the group of people.

15. The method of claim 12 wherein the mental state information includes mental state information from other players of the multiplayer game.

16. The method of claim 12 further comprising aggregating the mental state information on a plurality of people who play the multiplayer game.

17. The method of claim 16 wherein aggregated mental state information, generated in the aggregating, is used in the modifying of the game.

18. The method of claim 1 wherein the analyzing the mental state data comprises:
identifying a face of the individual;
determining regions within the face of the individual; and
evaluating the regions for emotional content.

19. The method of claim 1 further comprising
collecting second mental state data from a second individual involved in the game; and
analyzing the second mental state data to produce second mental state information from the second individual; and
wherein the modifying the game is further based on the second mental state information.

20. The method of claim 19 further comprising:
identifying a second face where the second face corresponds to the second individual;
determining regions within the second face of the second individual; and
evaluating the regions within the second face for emotional content.

21. The method of claim 1 further comprising sharing the mental state information across a social network.

22. The method of claim 21 wherein the sharing is used in rating for games and where the sharing includes information on affect that indicates a level of engagement.

23. The method of claim 1 wherein the modifying the game further includes modifying a single avatar that represents a group of people who are playing the game based on a collective mental state for the group of people.

24. The method of claim 1 further comprising applying a handicap to the mental state information to equalize opportunities for the individual in the game based on one or more other individuals in the game being determined to be of a different skill level from the individual.

25. The method of claim 1 further comprising:
identifying a facial expression in the facial data as an unusual facial expression for the individual; and
displaying the unusual facial expression within a gaming environment.

26. A computer program product stored on a non-transitory computer-readable medium for gaming, the computer program product comprising:
code for collecting mental state data, wherein the mental state data includes facial data, captured by a webcam, of an individual while the individual is involved in a game;
code for analyzing the mental state data to produce mental state information; and
code for modifying the game based on the mental state information, wherein the modifying the game includes changing tasks with which the individual is presented, based on a threshold, wherein the threshold represents a norm for a demographic of the individual, and wherein the modifying the game further includes modifying an avatar that represents the individual.

27. A computer system for gaming comprising:
a memory for storing instructions;
one or more processors attached to the memory wherein the one or more processors are configured to:
collect mental state data, wherein the mental state data includes facial data, captured by a webcam, of an individual while the individual is involved in a game;
analyze the mental state data to produce mental state information; and
modify the game based on the mental state information, wherein the modifying the game includes changing tasks with which the individual is presented, based on a threshold, wherein the threshold represents a norm for a demographic of the individual, and wherein the modifying the game further includes modifying an avatar that represents the individual.

* * * * *